United States Patent
Branch et al.

(10) Patent No.: US 11,065,130 B2
(45) Date of Patent: *Jul. 20, 2021

(54) EXPANDABLE SPINAL IMPLANT SYSTEM AND METHOD OF USING SAME

(71) Applicant: WARSAW ORTHOPEDIC, INC., Warsaw, IN (US)

(72) Inventors: Charles Branch, Advance, NC (US); Charles Fisher, Vancouver (CA); Mladen Djurasovic, Louisville, KY (US); Marcel Dvorak, Vancouver (CA); Sigurd Berven, San Francisco, CA (US); Anthony J. Melkent, Germantown, TN (US); Jonathan M. Dewey, Memphis, TN (US); Keith E. Miller, Germantown, TN (US); Adriaan J. Kuyler, Germantown, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/295,714

(22) Filed: Mar. 7, 2019

(65) Prior Publication Data

US 2019/0201209 A1    Jul. 4, 2019

Related U.S. Application Data

(62) Division of application No. 15/340,770, filed on Nov. 1, 2016, now Pat. No. 10,238,503.

(51) Int. Cl.
*A61F 2/44* (2006.01)
*A61F 2/46* (2006.01)
(Continued)

(52) U.S. Cl.
CPC .............. *A61F 2/447* (2013.01); *A61F 2/28* (2013.01); *A61F 2/4455* (2013.01);
(Continued)

(58) Field of Classification Search
CPC .......... A61F 2/44; A61F 2/447; A61F 2/4455; A61F 2/4465; A61F 2/46; A61F 2/4611; A61F 2/28
See application file for complete search history.

(56) References Cited

U.S. PATENT DOCUMENTS 7,156,875 B2   1/2007 Michelson
8,062,375 B2   11/2011 Glerum et al.
(Continued)

FOREIGN PATENT DOCUMENTS

WO   2001095838   12/2001
WO   2004019829   3/2004
(Continued)

OTHER PUBLICATIONS

Office Action and Search Report dated Sep. 4, 2019 for Chinese Application No. 201680060118.0.
(Continued)

*Primary Examiner* — Christopher J Beccia

(57) ABSTRACT

An expandable spinal implant includes a distal projection extending from only one side of the implant, ending in an anterior tip, the anterior portion and anterior tip defining an elongated distal end hook, which is wider than the proximal end. The distal end hook rotates around the spinal cord, aligning the implant with a desired pathway, then inserts into place in the disc space between the vertebrae. The elongated widened distal end hook provides a TLIF approach, distributes loads, provides anterior rim engagement, and creates lordosis.

20 Claims, 32 Drawing Sheets

(51) Int. Cl.
  *A61F 2/28*   (2006.01)
  *A61F 2/30*   (2006.01)
  *B33Y 80/00*  (2015.01)

(52) U.S. Cl.
  CPC .......... *A61F 2/4465* (2013.01); *A61F 2/4601* (2013.01); *A61F 2/4611* (2013.01); *A61F 2002/2817* (2013.01); *A61F 2002/30092* (2013.01); *A61F 2002/30133* (2013.01); *A61F 2002/30168* (2013.01); *A61F 2002/30304* (2013.01); *A61F 2002/30405* (2013.01); *A61F 2002/30471* (2013.01); *A61F 2002/30507* (2013.01); *A61F 2002/30537* (2013.01); *A61F 2002/30538* (2013.01); *A61F 2002/30556* (2013.01); *A61F 2002/30579* (2013.01); *A61F 2002/30593* (2013.01); *A61F 2002/30841* (2013.01); *A61F 2002/448* (2013.01); *A61F 2002/4627* (2013.01); *A61F 2002/4629* (2013.01); *A61F 2310/00017* (2013.01); *A61F 2310/00023* (2013.01); *A61F 2310/00029* (2013.01); *A61F 2310/00293* (2013.01); *A61F 2310/00359* (2013.01); *A61F 2310/00407* (2013.01); *A61F 2310/00796* (2013.01); *A61F 2310/00976* (2013.01); *B33Y 80/00* (2014.12)

(56) References Cited

U.S. PATENT DOCUMENTS

| | | | |
|---|---|---|---|
| 8,092,464 B2 | 1/2012 | McKay | |
| 8,556,979 B2 | 10/2013 | Glerum et al. | |
| 10,238,503 B2 * | 3/2019 | Branch | A61F 2/4465 |
| 2006/0253201 A1 | 11/2006 | McLuen | |
| 2011/0172774 A1 | 7/2011 | Varela | |
| 2011/0208309 A1 | 8/2011 | Peterson et al. | |
| 2012/0059470 A1 | 3/2012 | Weiman | |
| 2012/0158147 A1 | 6/2012 | Glerum | |
| 2013/0158664 A1 | 6/2013 | Palmatier | |
| 2013/0158669 A1 | 6/2013 | Sungarian et al. | |
| 2014/0100662 A1 | 4/2014 | Patterson et al. | |
| 2014/0228955 A1 | 8/2014 | Weiman | |
| 2014/0249630 A1 | 9/2014 | Weiman | |
| 2014/0343678 A1 | 11/2014 | Suddaby et al. | |
| 2015/0025636 A1 | 1/2015 | Lim et al. | |
| 2015/0100128 A1 | 4/2015 | Glerum et al. | |
| 2015/0173917 A1 | 6/2015 | Radcliffe et al. | |
| 2015/0216670 A1 | 8/2015 | Davenport et al. | |
| 2015/0272743 A1 | 10/2015 | Jimenez et al. | |
| 2015/0272746 A1 | 10/2015 | Jimenez et al. | |
| 2016/0120660 A1 | 5/2016 | Melkent et al. | |

FOREIGN PATENT DOCUMENTS

| | | |
|---|---|---|
| WO | 2008155472 | 12/2008 |
| WO | 2010148112 | 12/2010 |
| WO | WO 2015/085111 | 11/2015 |

OTHER PUBLICATIONS

Office Action dated Dec. 15, 2020 for Chinese Application 201711026763.3.

Search Reported dated Mar. 19, 2018 for EP Application No. 17195932.3.

Extended Search Reported dated Mar. 23, 2018 for EP Application No. 17195932.3.

* cited by examiner

EXPANDABLE SPINAL IMPLANT SYSTEM AND METHOD OF USING SAME

CROSS-REFERENCE TO RELATED APPLICATIONS

This application is a divisional of U.S. application Ser. No. 15/340,770, filed Nov. 1, 2016; all of which is incorporated by reference herein.

TECHNICAL FIELD

The present disclosure generally relates to medical devices for the treatment of musculoskeletal disorders, and more particularly to a surgical system that includes an expandable spinal implant, systems for implanting an expandable spinal implant, and a method for treating a spine.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, correction, discectomy, laminectomy and implantable prosthetics. As part of these surgical treatments, spinal constructs, such as, for example, bone fasteners, spinal rods and interbody devices can be used to provide stability to a treated region. For example, during surgical treatment, interbody devices may be introduced to a space between adjacent vertebral bodies (the interbody space) to properly space the vertebral bodies and provide a receptacle for bone growth promoting materials.

More recently, interbody devices have been introduced that provide additional capability beyond static spacing of the vertebral bodies. For example, some devices have expansion capability such that the implant may be introduced to the interbody space in a collapsed state and then expanded to produce additional spacing and, in some cases, introduce or restore curvature to the spine by expanding selectively on only one end or portion of the implant. However, many existing expandable interbody designs utilize internal mechanisms that may inhibit the introduction of bone growth promoting material into the interbody implant by a surgeon after the implant is expanded.

An additional problem exists related to subsidence of spinal surfaces due to existing interbody devices having inadequately-sized load-bearing surfaces. In the case of expandable devices, the loads on the load-bearing surfaces, including loads generated during expansion of the implant, are often significant. An expandable implant with relatively large surface areas is needed to bear the loads, including the loads generated during implant expansion, in an attempt to avoid a need for follow-on surgery due to subsidence of spinal surfaces.

The present invention seeks to address this and other shortcomings in the existing art.

SUMMARY

In one embodiment, an expandable spinal implant is provided deployable between a collapsed position and an expanded position in a disc space between upper and lower vertebral bodies. The implant includes a frame comprising a proximal wall, lateral walls, and a distal wall, wherein the proximal wall defines a proximal aperture and the distal wall defines a distal aperture. The implant also includes a plug movably disposed in the distal aperture of the frame and first and second endplates operably engaged with the frame and configured to expand outward from the frame when the plug is moved in a distal direction relative to the frame, each of the first and second endplates including respective first and second lateral walls and respective distal ends.

In one alternative embodiment a system is provided including an expandable spinal implant and an insertion instrument. The insertion instrument comprises a cannulated outer shaft and a driver shaft removably and rotatably disposed within the cannulated outer shaft. The expandable spinal implant comprises a frame with a proximal wall and a distal wall, wherein the proximal wall defines a proximal aperture and the distal wall defines a distal aperture. The proximal wall of the frame is configured to receive a distal end of the cannulated outer shaft for manipulating the expandable spinal implant. The expandable spinal implant also comprises a movable plug disposed in the distal aperture of the frame, wherein the plug comprises an interface configured to be operably engaged by a distal end of the driver shaft to move the plug relative to the frame. The expandable spinal implant also comprises first and second endplates engaged with the frame and configured to move relative to the frame when the plug is moved by the driver shaft of the insertion instrument. The driver shaft is also configured to be removable from the cannulated outer shaft of the insertion instrument such that after the plug has been moved distally relative to the frame, a bone growth promoting material may be introduced into the frame through the cannulated outer shaft of the insertion instrument.

In one alternative embodiment, each of the first and second endplates include an anterior portion projecting from the first and second lateral walls at the respective distal ends thereof. The projecting anterior portions increase the surface area of the respective endplates, and end in respective anterior tips. When the implant is in the collapsed position, the anterior portions and the anterior tips define a distal end hook portion. In addition, when the implant is in the collapsed position, the first endplate distal end and the second endplate distal end define a distal end beveled portion. The distal end hook portion has a greater width than the proximal end of the implant. The distal end hook portion is configured, upon insertion of the implant into the disc space, to hook at least partially around the vertebral foramen, thereby avoiding interference with the spinal cord, and other neural elements located within the vertebral foramen. The distal end hook portion is further configured, upon insertion into the disc space, to rotate to a TLIF/transverse pathway. The implant is now positioned to be inserted to the anterior apophyseal rims of each of the upper and lower vertebral bodies. Upon expansion of the implant, the distal hook end portion and the distal beveled end portion engage substantially the entire anterior apophyseal rim of each of the upper and lower vertebrae. Rows of teeth provided on the first endplate and on the second endplate prevent inadvertent backing out of the implant from the anterior apophyseal rims. The additional surface area and the additional width of at least the distal end hook portion enables the endplates to bear significantly greater loads applied to the implant by the upper and lower vertebrae. The distal end hook configuration enables a single implant to be positioned across the midline of the disc space, a single implant to be positioned spaced laterally to one side of the midline of the disc space, or a first implant to be positioned spaced laterally to one side of the midline of the disc space and a second implant to be positioned spaced laterally to the opposite side of the midline of the disc space.

In one embodiment, the distal beveled end surface connects to the lateral walls of the endplates opposite the position of the distal end hook portion via a curved portion. The curved portion allows the implant to achieve increased lateral contact with bone close to the anterior apophyseal rim.

In some embodiments, various other implants, systems and methods are disclosed.

BRIEF DESCRIPTION OF THE DRAWINGS

The present disclosure is further informed by the specific description accompanied by the following drawings, in which.

DETAILED DESCRIPTION

Figure 1:
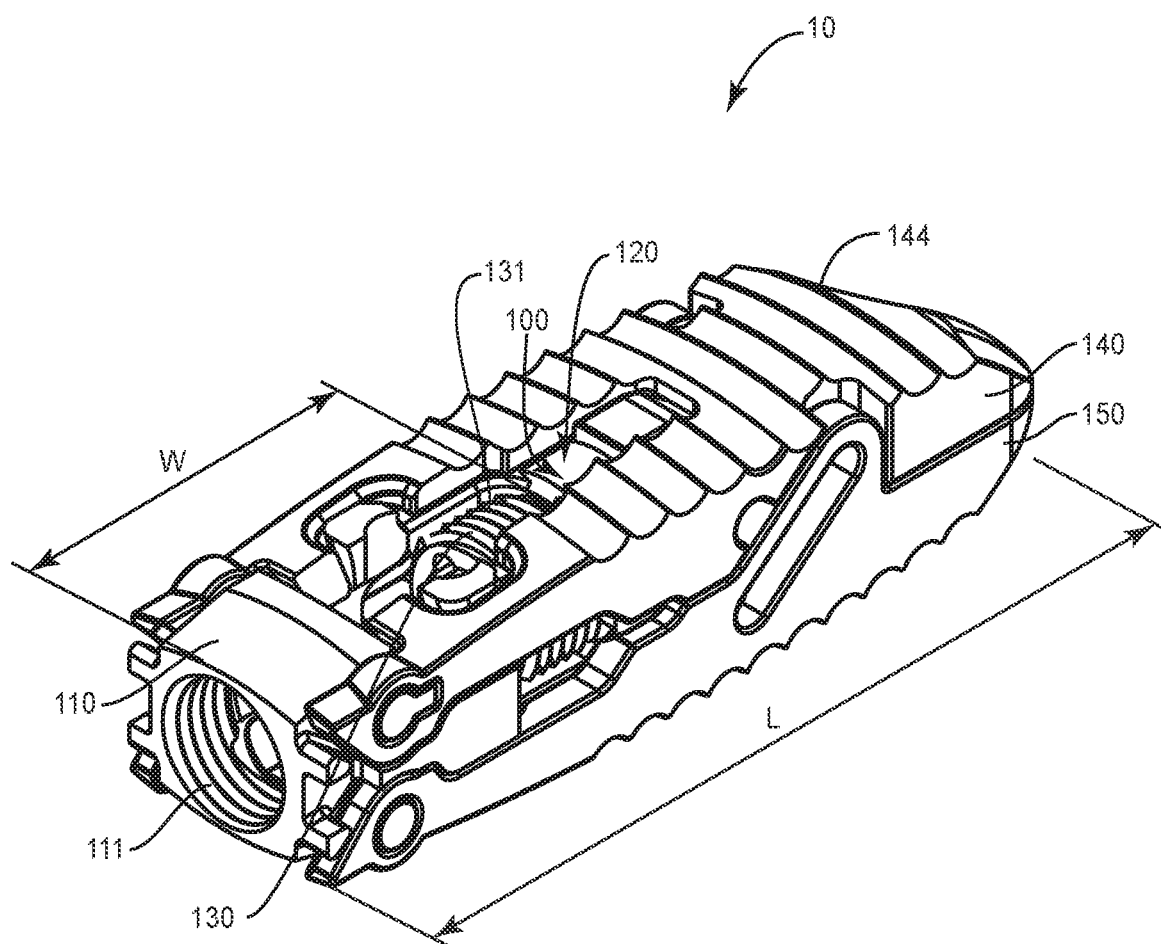
FIG. 1 is a perspective view of one embodiment of an expandable spinal implant system in a closed configuration in accordance with the principles of the present disclosure.

The exemplary embodiments of the surgical system and related methods of use disclosed are discussed in terms of medical devices for the treatment of musculoskeletal disorders and more particularly, in terms of an expandable surgical implant system that may include an expandable spinal implant, an insertion instrument and/or a method for treating a spine.

In some embodiments, the present system includes an expandable spinal implant system suitable for insertion from a direct posterior (sometimes referred to as PLIF procedures) in pairs or singularly and then expandable at a distal end in order to impart and/or augment a lordotic curve of the spine. In some embodiments shown herein, the expandable spinal implant system may also be configured for use in oblique, postero-lateral procedures and/or transforaminal lumbar interbody fusions (sometimes referred to as TLIF procedures). Additionally, the frame disclosed in various embodiments may be configured to place a movable plug of the spinal implant in a substantially distal position within the spinal implant so as to clear a proximal volume within the implant for packing with bone-growth promoting materials after the implant has been inserted and/or expanded using the various techniques described herein. The frame and other various spinal implant components may also be configured with one or more sidewalls and/or openings to direct bone-growth promoting material to a selected area of an intervertebral or interbody space after the insertion and/or deployment of the spinal implant. In some embodiments, the spinal implant system may also be provided with a tapered distal tip (as viewed from a superior or top surface) such that the implant is shaped for insertion from an oblique approach and placement at a diagonal across an intervertebral or interbody space.

In some embodiments, the spinal implant system may also be employed to restore and/or impart sagittal balance to a patient by increasing and/or restoring an appropriate lordotic angle between vertebral bodies at a selected level where the spinal implant is implanted and expanded. In some embodiments, a pair of such spinal implants may be employed from bilateral PLIF approaches and expanded to differing heights to impart and/or restore both a lordotic angle as well as align the spine in the coronal plane (so as to treat a scoliotic curvature, for example). In some embodiments, a single such spinal implant may be employed from a postero-lateral TLIF approach and expanded to differing heights to impart and/or restore both a lordotic angle as well as align the spine in the coronal plane (so as to treat a scoliotic curvature, for example). In the various embodiments described, the spinal implant system may be useful in a variety of complex spinal procedures for treating spinal conditions beyond one-level fusions. Furthermore, the spinal implant system described in the enclosed embodiments may also be used as a fusion device with an expandable height for tailoring the implant to a particular interbody disc space to restore the spacing between adjacent vertebral bodies and facilitate spinal fusion between the adjacent vertebral bodies.

In some embodiments, and as mentioned above, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed spinal implant system may be alternatively employed in a surgical treatment with a patient in a prone or supine position, and/or employ various surgical approaches to the spine, including anterior, posterior, posterior mid-line, direct lateral, postero-lateral oblique, and/or antero lateral oblique approaches, and in other body regions. The present disclosure may also be alternatively employed with procedures for treating the lumbar, cervical, thoracic, sacral and pelvic regions of a spinal column. The spinal implant system of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs, biologics, bone grafts (including allograft, autograft, xenograft, for example) or bone-growth promoting materials to a patient (human, normal or otherwise or other mammal), employing implantable devices, and/or employing instruments that treat the disease, such as, for example, micro-discectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise. The term "bone growth promoting material" as used herein may include, but is not limited to: bone graft (autograft, allograft, xenograft) in a variety of forms and compositions (including but not limited to morselized bone graft); osteoinductive material such as bone morphogenetic proteins (BMP) (including but not limited to INFUSE® available from Medtronic plc) and alternative small molecule osteoinductive substances; osteoconductive materials such as demineralized bone matrix (DBM) in a variety of forms and compositions (putty, chips, bagged (including but not limited to the GRAFTON® family of products available from Medtronic plc)); collagen sponge; bone putty; ceramic-based void fillers; ceramic powders; and/or other substances suitable for inducing, conducting or facilitating bone growth and/or bony fusion of existing bony structures. Such bone growth promoting materials (denoted "BG" in some Figures herein) may be provided in a variety of solids, putties, liquids, colloids, solutions, or other preparations suitable for being packed or placed into or around the various implant 10, 20 embodiments described herein.

The following discussion includes a description of a surgical system including one or more spinal implants, related components and methods of employing the surgical system in accordance with the principles of the present disclosure. Various alternate embodiments are disclosed and individual components of each embodiment may be used with other embodiments. Reference is made in detail to the exemplary embodiments of the present disclosure, which are illustrated in the accompanying figures. Turning to FIGS. 1-12, there are illustrated components of a surgical system, such as, for example, an expandable spinal implant 10, 20 and associated system including an insertion instrument 30.

The components of expandable spinal implant system 10, 20, 30 can be fabricated from biologically acceptable materials suitable for medical applications, including metals, synthetic polymers, ceramics and bone material and/or their composites. For example, the components of expandable spinal implant system (including, but not limited to implant 10, implant 20, insertion instrument 30), individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO.sub.4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may be formed or constructed material composites, including the above materials, to achieve various desired characteristics such as strength, rigidity, elasticity, compliance, biomechanical performance, durability and radiolucency or imaging preference. The components of expandable spinal implant system 10, 20, 30, individually or collectively, may also be fabricated from a heterogeneous material such as a combination of two or more of the above-described materials. The components of expandable spinal implant system 10, 20, 30 may be monolithically formed, integrally connected or include fastening elements and/or instruments, as described herein. For example, in some embodiments expandable spinal implant system 10, 20, 30 may comprise expandable spinal implants 10, 20 comprising PEEK and/or titanium structures with radiolucent markers (such as tantalum pins and/or spikes) selectively placed in the implant to provide a surgeon with placement and/or sizing information when the expandable spinal implant 10, 20 is placed in the spine. The components of expandable spinal implant system 10, 20, 30 may be formed using a variety of subtractive and additive manufacturing techniques, including, but not limited to machining, milling, extruding, molding, 3D-printing, sintering, coating, vapor deposition, and laser/beam melting. Furthermore, various components of the expandable spinal implant system 10, 20, 30 may be coated or treated with a variety of additives or coatings to improve biocompatibility, bone growth promotion or other features. For example, the endplates 140, 150, 240, 250 may be selectively coated with bone growth promoting or bone ongrowth promoting surface treatments that may include, but are not limited to: titanium coatings (solid, porous or textured), hydroxyapatite coatings, or titanium plates (solid, porous or textured).

Expandable spinal implant system 10, 20, 30 may be employed, for example, with a minimally invasive procedure, including percutaneous techniques, mini-open and open surgical techniques to deliver and introduce instrumentation and/or one or more spinal implants at a surgical site within a body of a patient, for example, a section of a spine. In some embodiments, expandable spinal implant system 10, 20, 30 may be employed with surgical procedures, as described herein, and/or, for example, corpectomy, discectomy, fusion and/or fixation treatments that employ spinal implants to restore the mechanical support function of vertebrae. In some embodiments, expandable spinal implant system 10, 20, 30 may be employed with surgical approaches, including but not limited to: posterior lumbar interbody fusion (PLIF), oblique lumbar interbody fusion, transforaminal lumbar interbody fusion (TLIF), various types of anterior fusion procedures, and any fusion procedure in any portion of the spinal column (sacral, lumbar, thoracic, and cervical, for example). Exemplary use of the expandable spinal implant system 10, 20, 30 in PLIF and TLIF techniques is shown generally in FIGS. 13-17.

Figure 2:
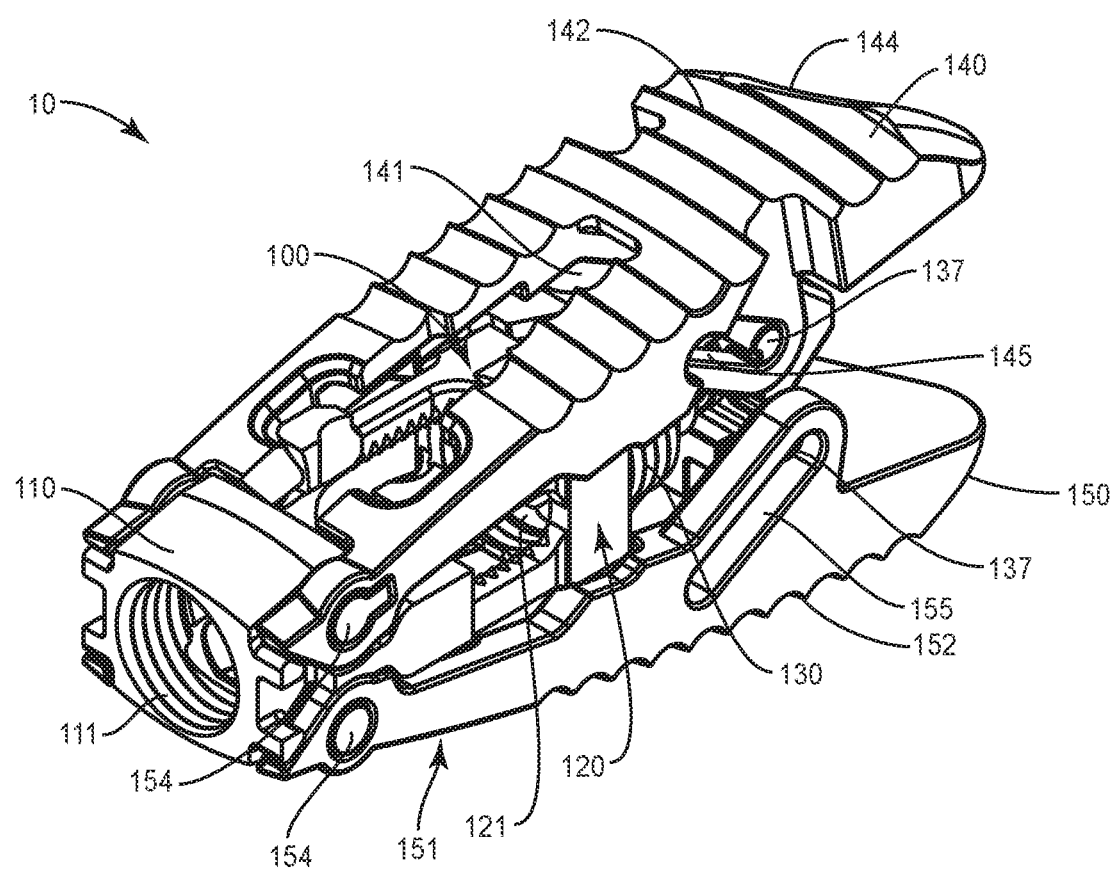
FIG. 2 is a perspective view one embodiment of an expandable spinal implant system in an open configuration in accordance with the principles of the present disclosure.

As shown generally in FIGS. 1-8, two exemplary embodiments of an expandable spinal implant 10, 20 are shown (implant 10 is highlighted in exemplary FIGS. 1-4 and implant 20 is highlighted in exemplary FIGS. 5-8). Referring to FIGS. 1 and 2, expandable spinal implant 10 may comprise a frame 100 comprising a proximal wall 110 and a distal wall 120. The frame 100 may provide a mechanism for placing an expansion mechanism distally in the implant 10 such that, once expanded, the implant 10 provides ample room nearer the proximal end of the implant (such as at least partially within the frame 100, for example) for the post-packing of bone growth promoting materials. For example, the proximal wall 110 of the frame 100 may define a proximal aperture 111 which may be suitable for receiving at least part of an insertion instrument 30 through which bone growth promoting material may be introduced into a proximal portion of the implant 10. Furthermore, the distal wall 120 of the frame may define a distal aperture 121 (see FIG. 2, for example) that is adapted to receive a plug 130. As described further herein, the plug 130 may be movably disposed in the distal aperture 121 of the frame.

A plunger, syringe, tamp, funnel, pistol grip or hydraulic means may optionally be used to advance the material down the insertion instrument 30 and into the implant 10 and/or disc space. Another alternative may include passing a tube down the insertion instrument 30. The tube in one preferred embodiment may be flexible and made of plastic or rubber. The tube may be prefilled with graft or other material and in one embodiment has a syringe attached at the end of the tube or alternatively includes a pistol grip, funnel or other means of advancing graft or other material down the tube. The syringe may be prefilled with material. The tube may be tapered at the distal end to facilitate interfacing the implant 10. The tube and or the insertion instrument 30 may be flared out at the proximal end to act as a funnel or to facilitate receiving a funnel, syringe, pistol grip, or other instrument for providing and delivering the material. The graft also may be loaded into the disc space, where disc material has been removed, prior to the insertion of the implant 10, by a tube such as disclosed in U.S. Pat. No. 8,092,464 to McKay, incorporated by reference herein in its entirety. The graft loading process described here and below is not necessarily limited to just use with the disclosed expandable implant but rather could be used in any fusion procedure or with the use of any intervertebral implant (lateral, oblique, ALIF, PLIF, etc.).

Figure 3:
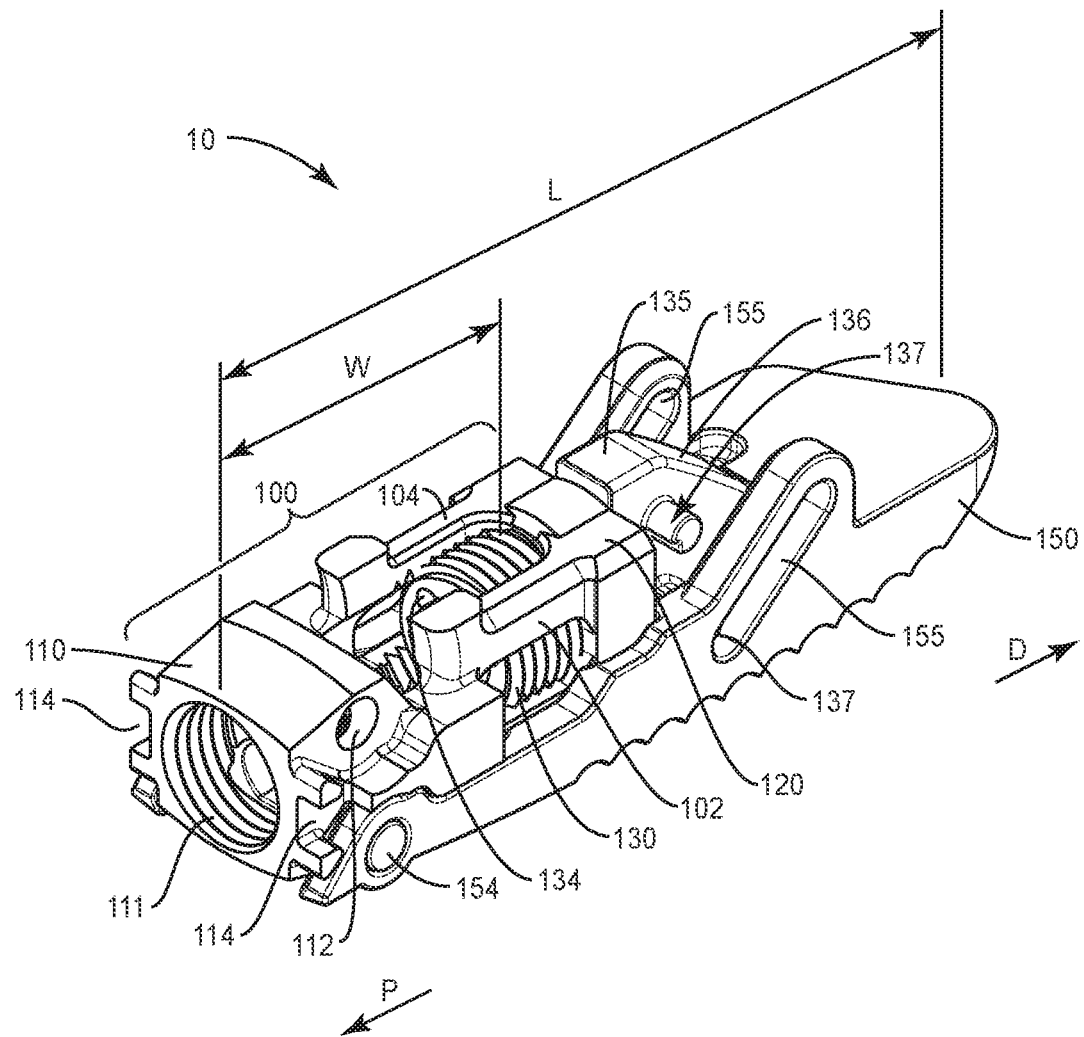
FIG. 3 is a perspective view of the components shown in FIG. 1 but with one endplate removed to show inner structures of a closed expandable spinal implant system in accordance with the principles of the present disclosure.
Figure 4:
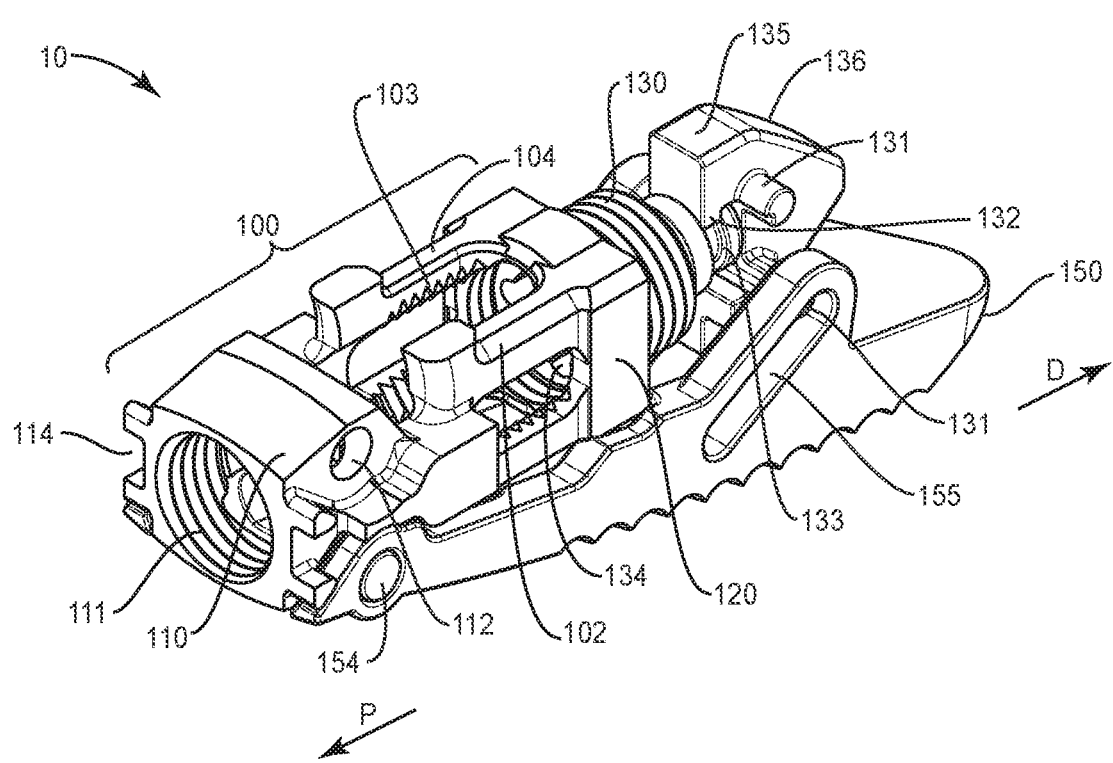
FIG. 4 is a perspective view of the components shown in FIG. 1 but with one endplate removed to show inner structures of an open expandable spinal implant system in accordance with the principles of the present disclosure.
Figure 5:
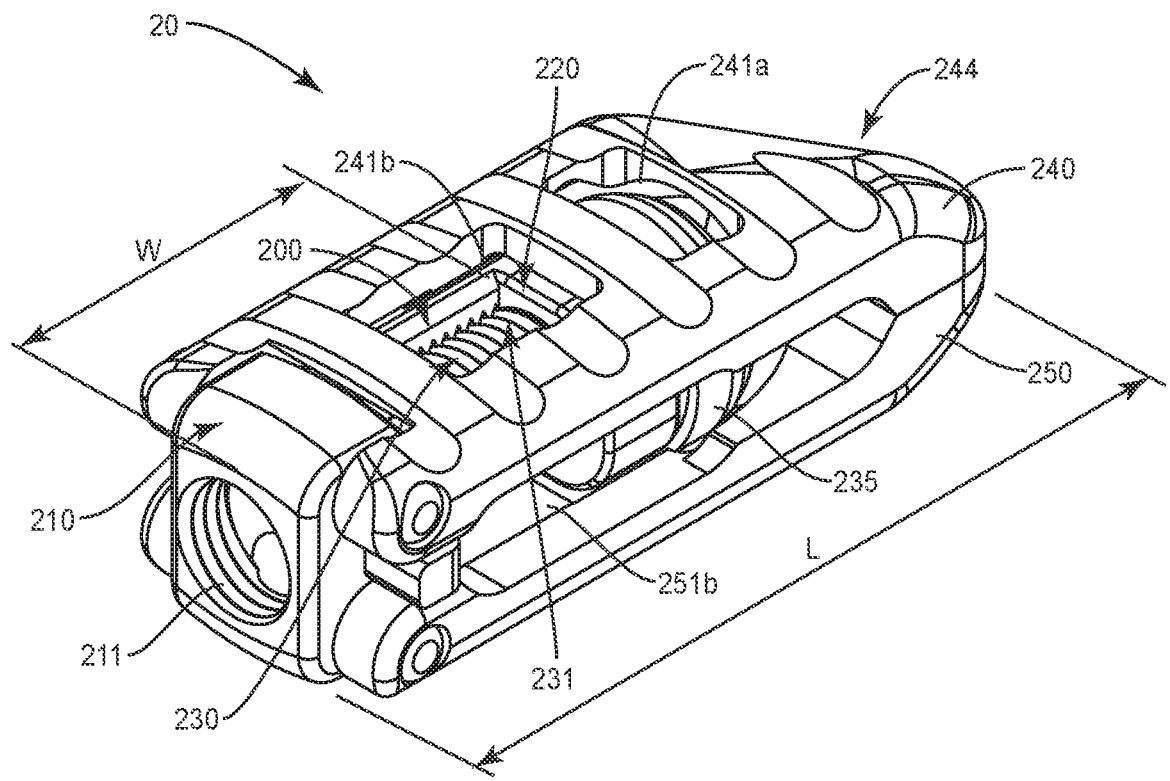
FIG. 5 is a perspective view of one embodiment of an expandable spinal implant system in a closed configuration in accordance with the principles of the present disclosure.
Figure 6:
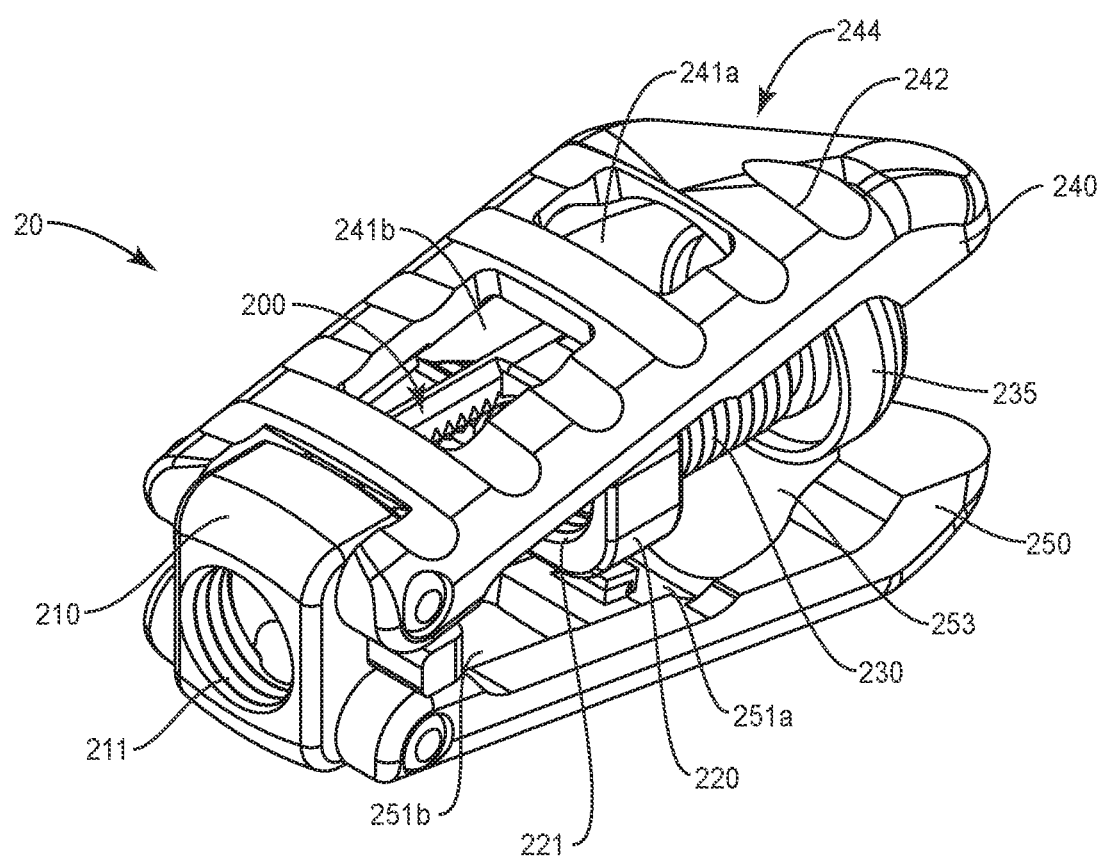
FIG. 6 is a perspective view one embodiment of an expandable spinal implant system in an open configuration in accordance with the principles of the present disclosure.
Figure 14:
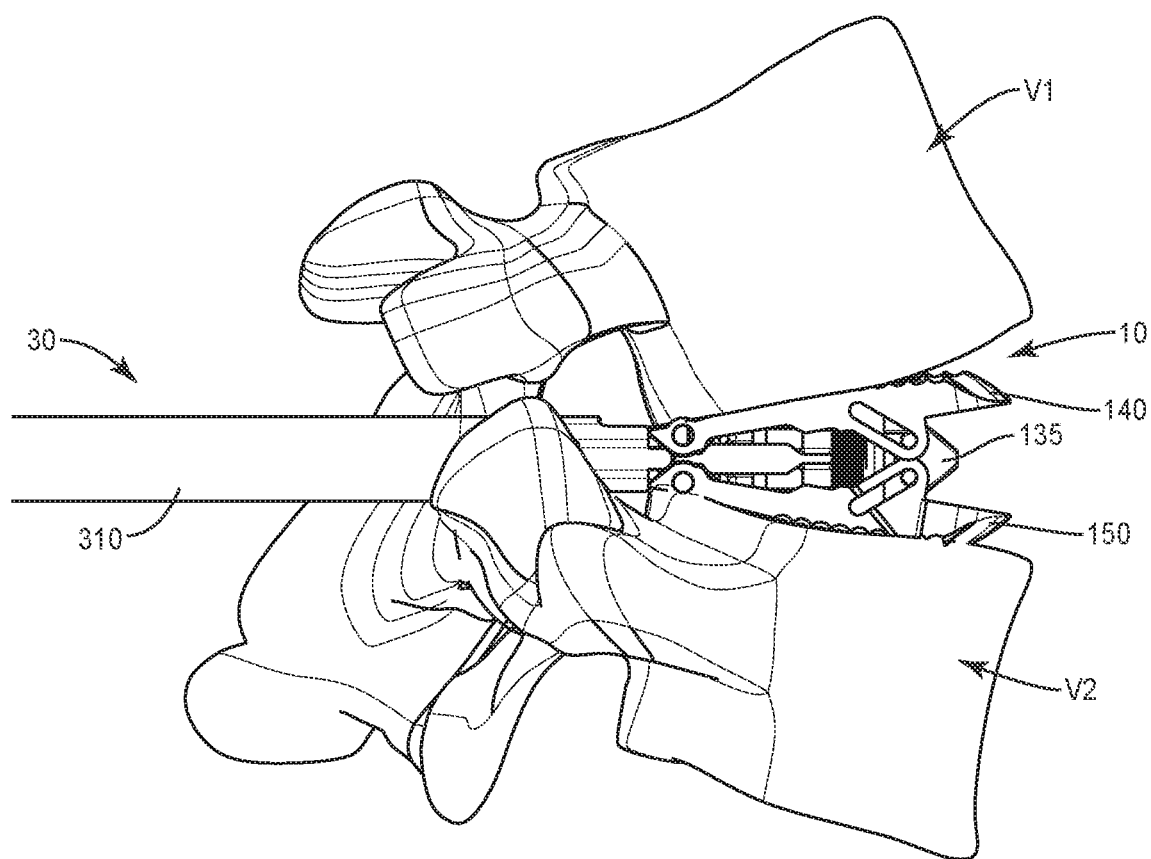
FIG. 14 is a perspective view of the components shown in FIG. 13 as used in a PLIF surgical procedure in accordance with the principles of the present disclosure.
Figure 16:
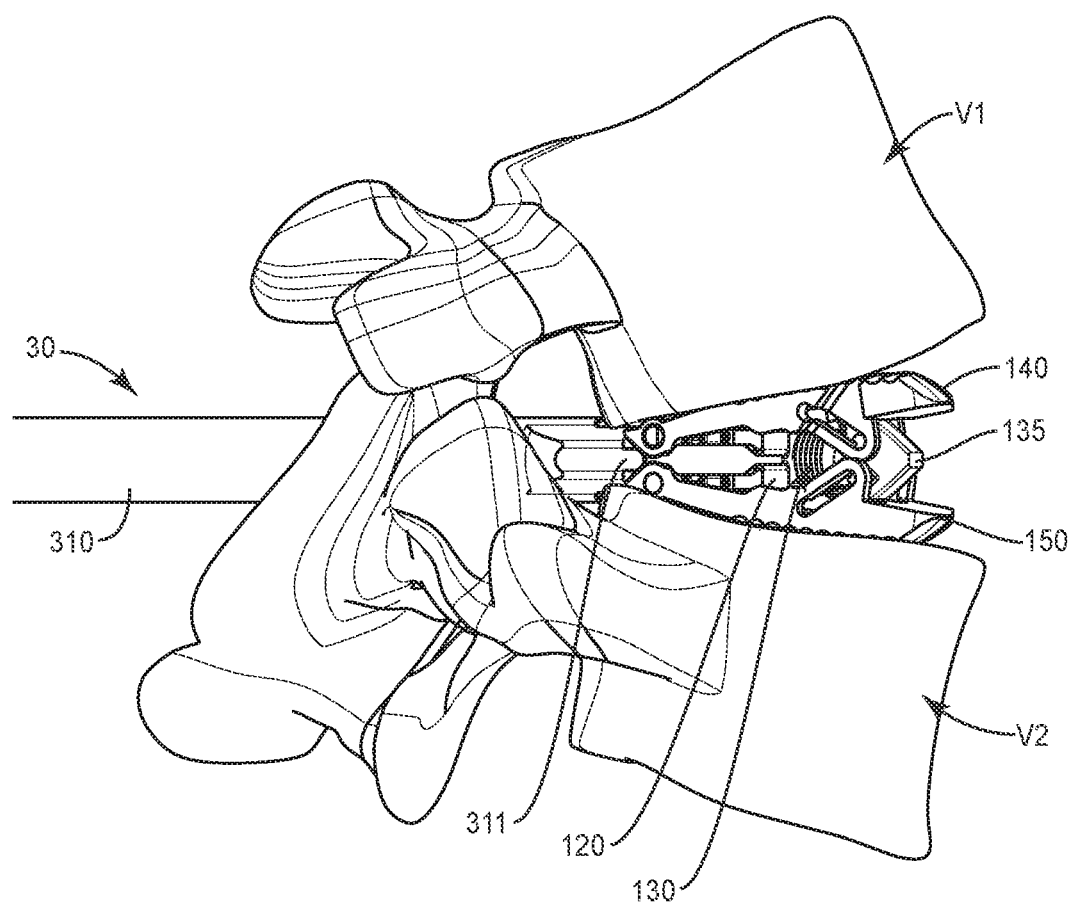
FIG. 16 is a perspective view of the components shown in FIG. 15 as used in a TLIF surgical procedure in accordance with the principles of the present disclosure.

The expandable spinal implant 10 may further comprise a first endplate 140 operably engaged with the frame 100 and configured to expand outward from the frame 100 when the plug 130 is moved in a distal direction D (See FIGS. 3-4). Furthermore, in some embodiments, the expandable spinal implant 10 may comprise opposing first and second endplates 140, 150 as shown generally in FIGS. 1 and 2. In some such embodiments of the expandable spinal implant 10, the second endplate 150 may be operably engaged with the frame 100 and configured to expand outward from the frame 100 when the plug 130 is moved in a distal direction D. Furthermore, as shown in FIG. 1, the second endplate 150 may be disposed about the frame 100 and opposing the first endplate 140, wherein the first endplate 140 and the second endplate 150 extend from a proximal end of the implant 10 to a distal end of the implant 10 (along the length L of the implant 10) and at least partially enclose the frame 100. A similar structure is also shown in implant 20 of FIGS. 5-8, wherein endplates 240, 250 cooperate to at least partially enclose the frame 200 (see FIG. 5, for example). The various endplates 140, 150, 240, 250 may be provided with convex surfaces in multiple planes to conform to adjacent vertebral body endplates (see V1, V2 as shown in FIGS. 14 and 16). It should be understood that the surfaces of the various endplates 140, 150, 240, 250 could also be constructed with a convexity in only one plane or without any convexities. Furthermore, the vertebral body V1, V2 contacting surfaces of endplates 140, 150, 240, 250 may be provided with various anti-migration and/or osseointegration features including, but not limited to: ridges, teeth, pores, and coatings (including but not limited to porous titanium coatings such as those provided on Capstone PTC™ implants available from Medtronic plc).

Figure 18:
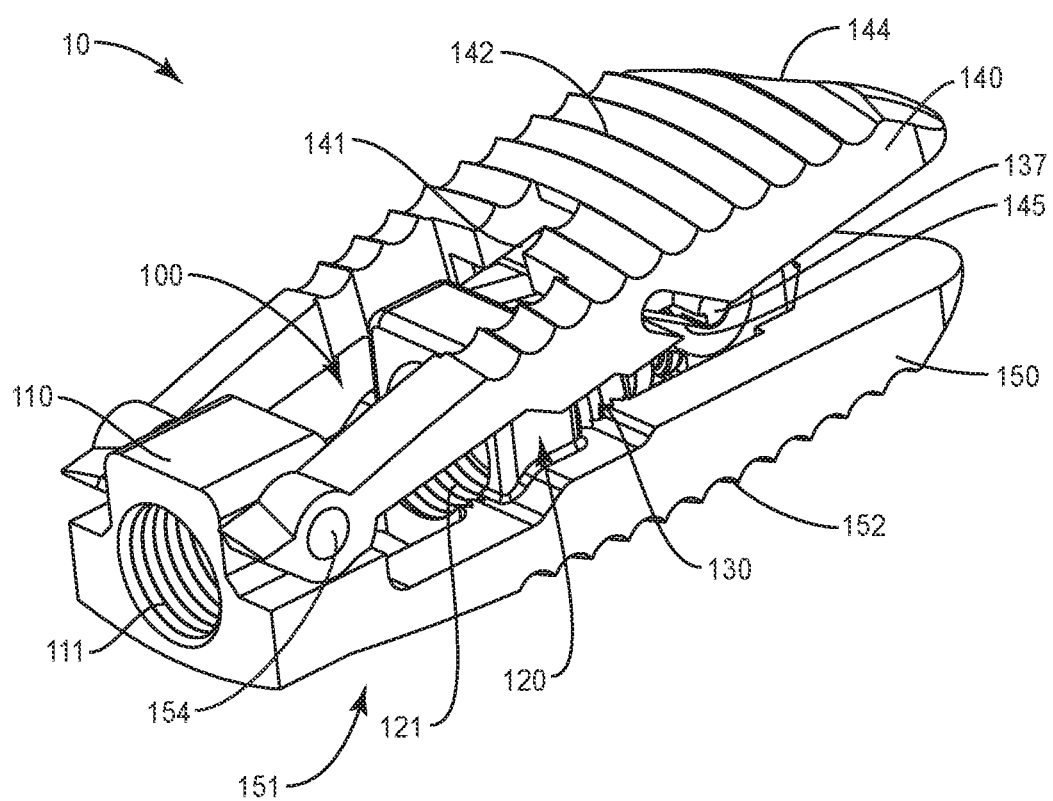
FIG. 18 is a perspective view of one embodiment of an expandable spinal implant system with a single movable endplate and wherein the frame may be substantially integral with at least one endplate.
Figure 19:
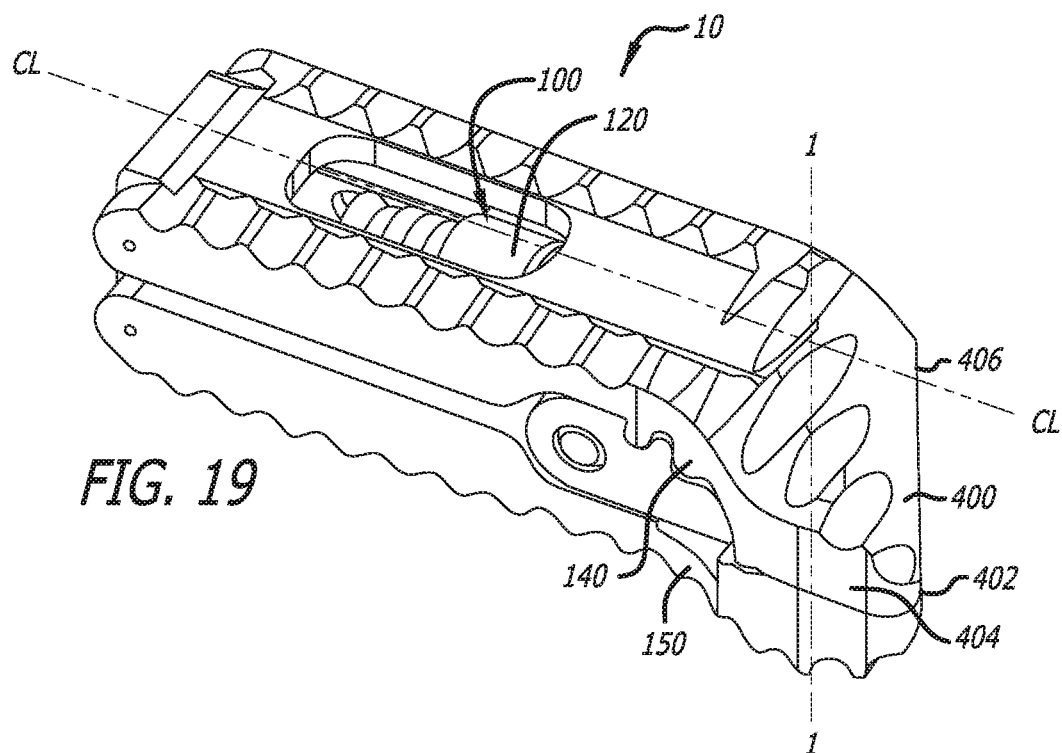
FIG. 19 is a perspective view of one embodiment of an expandable spinal implant having an anterior projection and an anterior tip defining a distal end hook portion.
Figure 20:
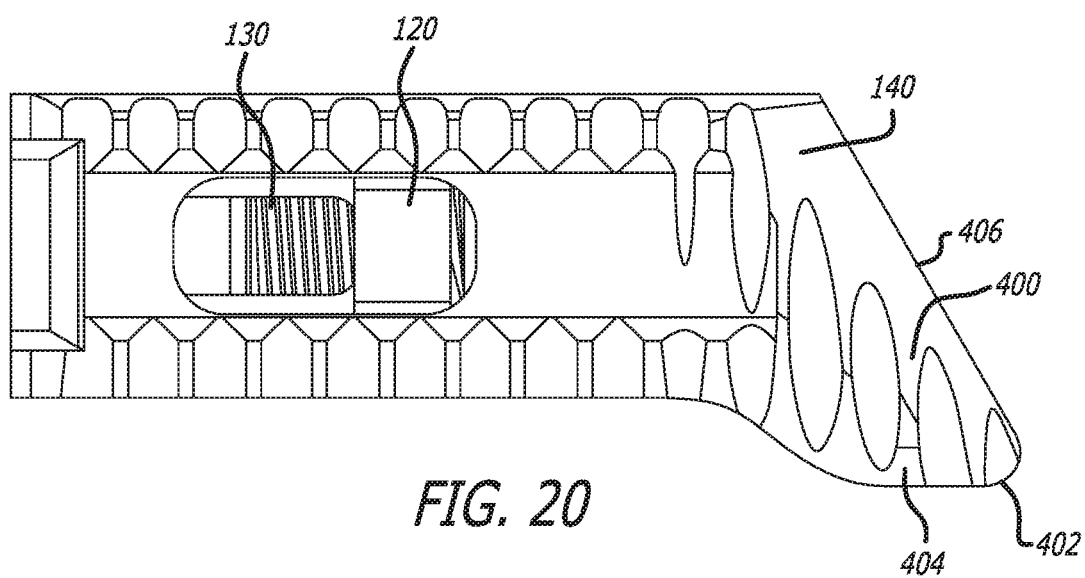
FIG. 20 is a top view of one embodiment of an expandable spinal implant having an anterior projection and an anterior tip defining a distal end hook portion.
Figure 21:
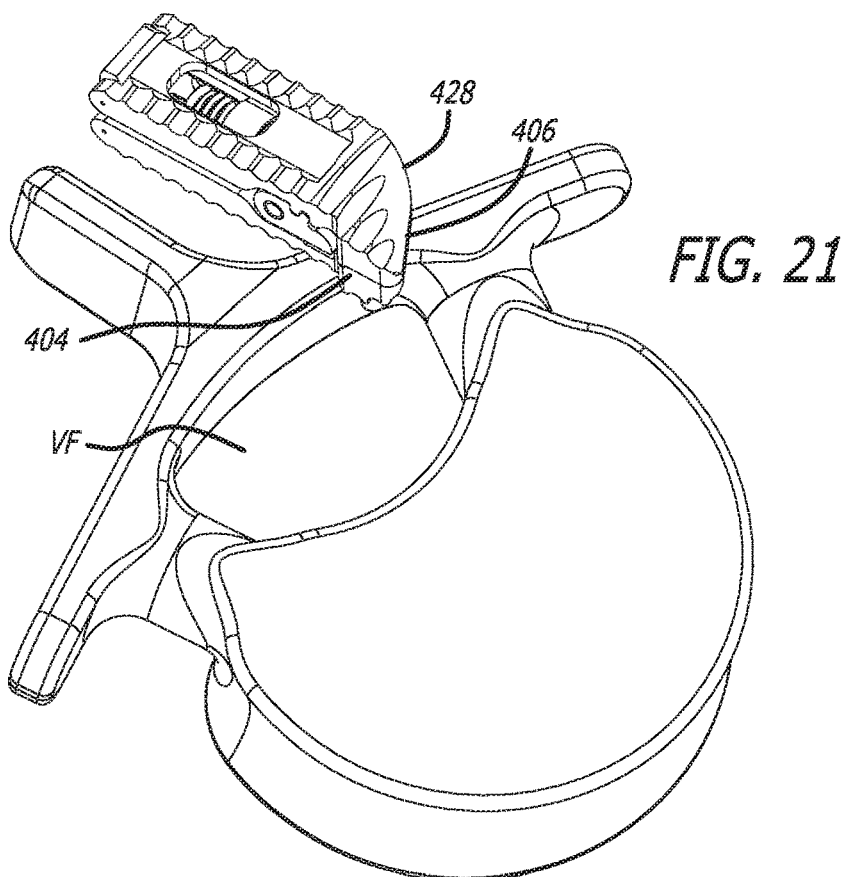
FIGS. 21 and 22 are perspective views depicting an initial insertion path into a disc space of one embodiment of an expandable spinal implant having an anterior projection and an anterior tip defining a distal end hook portion.
Figure 22:
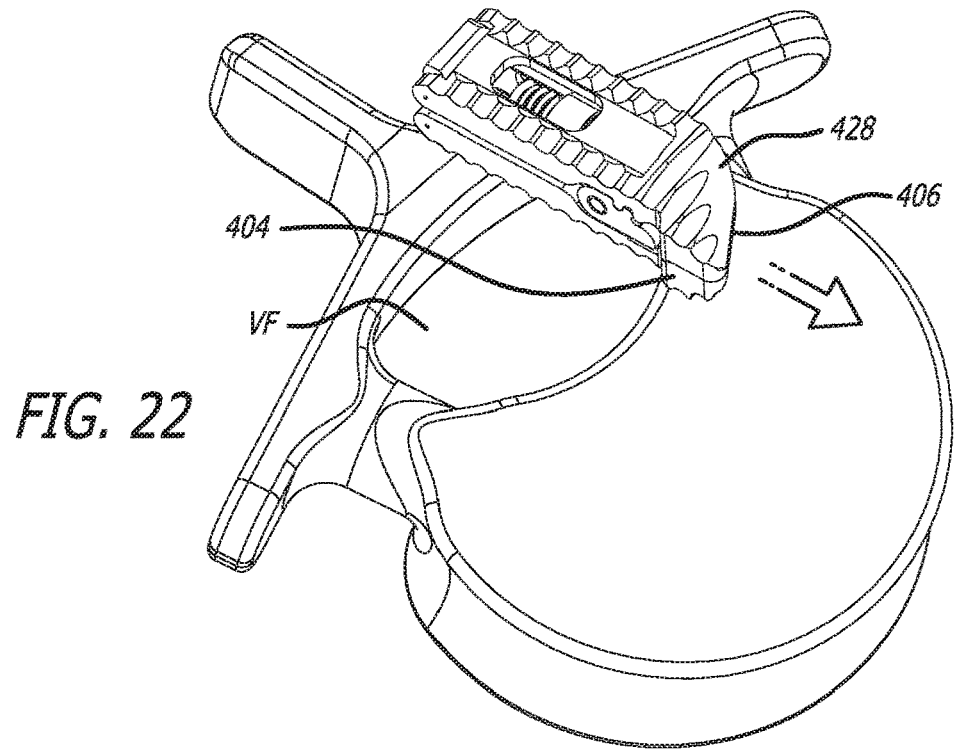

FIG. 18 shows an embodiment of an expandable spinal implant 10 comprising only a first endplate 140 operably engaged with the frame 100 and configured to expand outward from the frame 100 when the plug 130 is moved in a distal direction D (See FIGS. 3-4). In the embodiment of FIG. 18, the second endplate 150 may be integrally formed with the frame 100 and/or non-movable relative to the frame 100 such that as the plug 130 is moved distally, only the first endplate 140 (hinged to the frame 100 via pin 154). In such embodiments, the distal head portion 135 may be modified to engage the movable first endplate 140 and the static second endplate 150. For example, as shown generally in FIG. 3A, the movable first or second endplate 150 (and/or the complementary endplate 140) may comprise a ramped surface 153 upon which ramped surface 136 of the distal head portion 135 may bear as the implant 10 is expanded. The ramp 136/153 mechanism may cooperate with a paired lateral post 137 and track 145 system (see FIG. 18) in order to optimize the opening and/or expansion of the implant 10.

Referring generally to FIGS. 1-4, the endplates 140, 150 may be operably engaged with the frame 100 via a hinge mechanism located near or on the proximal wall 110 of the frame 100. For example, pins 154 may be provided that engage corresponding pin apertures 112 defined in the frame 100 such that the endplates are operably engaged with and/or hinged relative to the frame 100 such that the endplates 140, 150 may be expandable relative to the frame 100 by virtue of the cooperation of the pins 154 and pin apertures 112 as the plug 130 is moved distally D relative to the frame 100 of the implant 10. Similar hinge mechanisms are also shown relative to the embodiments of FIGS. 7 and 8 comprising pins 154 engaged with pin apertures 212 to connect frame 200 with endplates 240, 250 in a hinged relationship. While multi-part mechanical hinges are shown in some of the pictured embodiments, it should be understood that other types of hinge and/or connection mechanisms may also be used to operably engage the frame 100 with the expandable endplates 140, 150 of the implant. For example, in some embodiments, a "living hinge" may be utilized wherein the endplates 140, 150 are at least partially integrally formed with the frame 100 at the hinge point but with cut-outs or flex points that allow the endplates 140, 150 to rotate about the hinge connection. In summary, the frame 100 and endplates 140, 150 may be operably engaged in a number of different ways including but not limited to: integral connections, separable connections, mechanically fixed connections using fastener or adhesives, releasable connections (including, but not limited to keyways and partially open hinges), and other connection types. In some embodiments, the frame 100 and endplates 140, 150 may be integrally formed using additive manufacturing techniques such as 3D printing or sintering laser/beam melting, casting, extruding, or machined in an integral form using subtractive manufacturing techniques from one or more stock materials.

In some embodiments, the frame 100 of the expandable spinal implant 10 further comprises at least one side wall 102 engaged with the proximal wall 110 and the distal wall 120. As shown generally in FIG. 3, the side wall 102 or walls 102, 104 may be configured to space the proximal wall 110 and the distal wall 120 along a longitudinal axis (running substantially and/or nearly parallel to the length L) of the expandable spinal implant 10. The side walls 102, 104 may also be configured to contain bone growth promoting material in a proximal portion of the implant 10 that may be pre-packed or post-packed into the implant 10 via the proximal aperture 111. The side walls 102, 104 may cooperate with the proximal wall 110 and the distal wall 120 to create a four-sided frame 100 (that may define side apertures as shown in FIGS. 3-4). In some such embodiments, the frame may define internal threads 103 configured to cooperate with an outer threaded surface 131 of the plug 130 when the plug 130 is positioned generally proximally relative to the distal wall 120 of the frame 100.

The frame 100 may be especially useful in some embodiments for placing the plug 130 in a substantially distal position relative to the overall length L of the implant 10 such that a distal portion of the implant (within a volume substantially encompassed by the frame 100, for example) may be open and free to be filled (or "post-packed" with bone-growth promoting materials after the implant has been placed in a disc space between vertebral bodies (see, for example, the placement of implant 10, between vertebral bodies V1 and V2, shown in FIGS. 14 and 16). As described herein with respect to FIGS. 1, 3, 5 and 7, the implant 10, 20 may comprise or define a length L along a central longitudinal axis thereof, CL, extending from a proximal end 110 thereof to a distal end 144 thereof. In some such embodiments, the distal wall 120 of the frame may be disposed at least one third (⅓) of the length L (i.e. at a position spaced distally from the proximal end 110 by a distance W as shown generally in FIGS. 3 and 7). In other embodiments the distal wall 120 of the frame may be disposed at other fractions of the length L (i.e. at a position spaced distally from the proximal end 110 by a distance W as shown generally in FIGS. 3 and 7) including, but not limited to, at least ⅒, ⅛, ⅕, ¼, ¾, ⅞ and ⁹⁄₁₀. In other embodiments, the distal wall 120 of the frame may be disposed at a position spaced distally from the proximal end 110 by a distance W as shown generally in FIGS. 3 and 7 wherein the distance W ranges from 0 to 100 percent of the distance L, but in some instances distance W is at least 0.25 of the distance L to provide space in a proximal portion of the implant 10 for bone growth promoting material to be adequately post-packed into the area defined at least in part by distance W when the plug 130 is moved distally. Therefore a proximal portion of the implant 10 (such as an internal volume defined at least in part by frame 100) may be left substantially open and in fluid communication with the proximal aperture 111 of the frame 100 such that a bone growth promoting material may be placed through the proximal aperture 111 of the frame 100 after the plug 130 is moved in a distal direction D (see FIG. 3 showing the plug in an initial position, and FIG. 4 showing the plug moved distally to reveal a frame 100 volume left open and in fluid communication with the proximal aperture 111).

In other embodiments, as shown relative to the implant 20 in FIGS. 5-8, a single side wall 204 may replace the dual-wall embodiments of FIGS. 1-4 to space the distal wall 120 of the frame 100 from the proximal wall 110 of the frame. In some such embodiments with a single side wall 204, the frame 200 may be substantially open on one side of the implant 10 to allow for post-insertion packing of bone growth promoting material via the open side of the frame 200. The "open" or wall-less side of the frame 200 (which may be positioned generally opposite the side wall 204) may also be used to direct and/or contain bone growth promoting material that may be introduced to the implant implantation site through the proximal aperture 211 of the frame 200 of the implant 20. As with the "closed" embodiment having two side walls 102, 104, the single side wall 204 embodiments may also define internal threads 203 configured to cooperate with an outer threaded surface 231 of the plug 230 when the plug 230 is positioned generally proximally relative to the distal wall 220 of the frame 200.

Figure 3A:
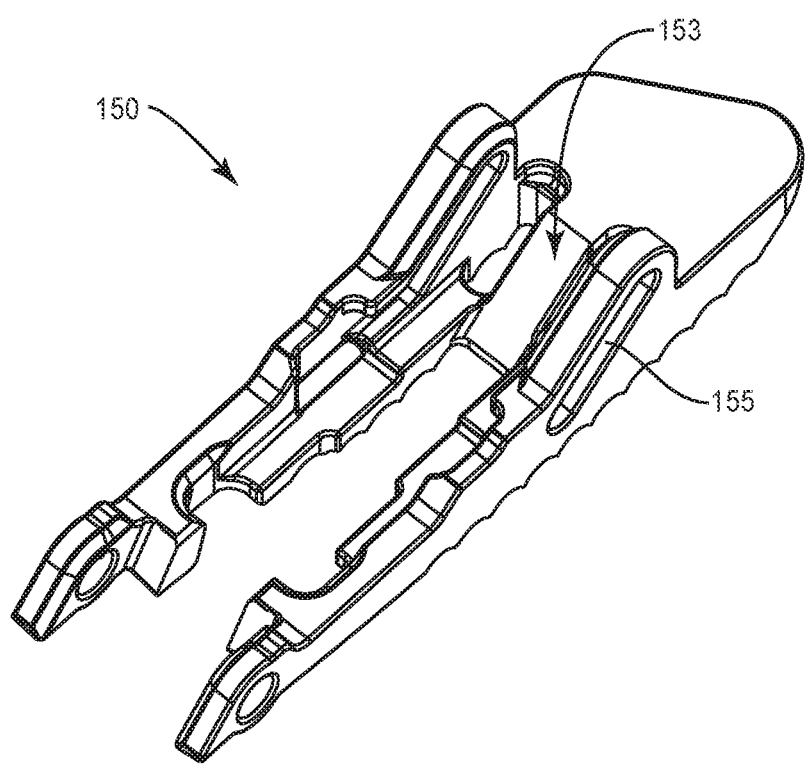
FIG. 3A is a perspective view of an endplate component in accordance with the principles of the present disclosure.
Figure 8:
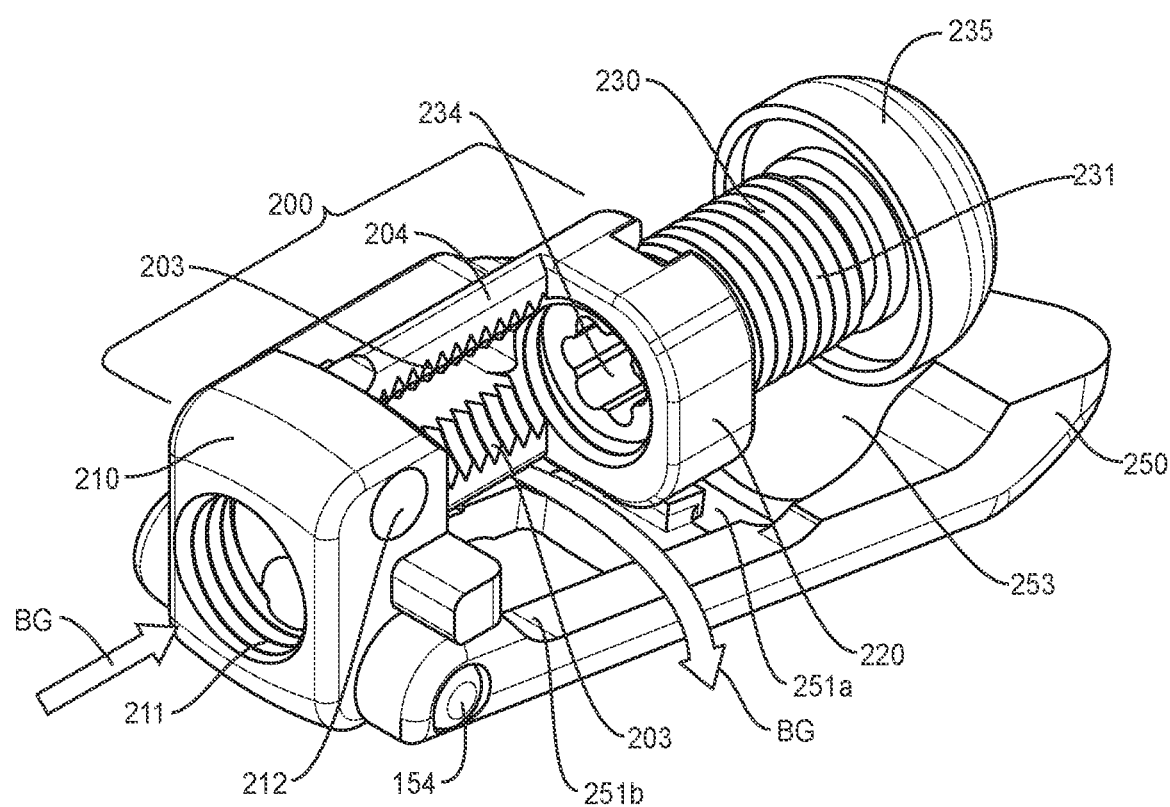
FIG. 8 is a perspective view of the components shown in FIG. 6 but with one endplate removed to show inner structures of an open expandable spinal implant system in accordance with the principles of the present disclosure.

In various embodiments, the plug 130, 230 provided in the expandable spinal implant 10, 20 may comprise a threaded outer surface 131 (see FIG. 1, for example), and the distal aperture 121 may comprise a complementary threaded inner surface operably engaged with the threaded outer surface 131 of the plug 130. The threaded outer surface 131 of the plug may be disposed on a proximal end of the plug 130 such that the plug 130 moves distally D as shown in FIG. 4 when the plug 130 is rotated relative to the distal wall 120 of the frame 100. In some embodiments, as shown generally in FIGS. 4 and 8, the frame 100 may comprise a sidewall 104 connecting the distal wall 120 and the proximal wall 110, wherein the at sidewall 104 comprises a sidewall threaded surface 103 configured to be operably engaged with the threaded outer surface 131 of the plug 130 (especially when the plug is still positioned proximally relative to the frame 100). An alternate embodiment of the sidewall threaded surface 203 is also shown in FIG. 8. Furthermore, the plug 130 may also comprise a distal head portion 135 configured to urge the endplate 140 away from the frame 100 with the plug 130 is moved in a distal direction D. The distal head portion 135 may be configured in some embodiments (as shown generally in FIGS. 1-4) with a separate structure having ramped surfaces 136 that may be configured to interface with complementary ramped surfaces on the endplates 140, 150. For example, as shown in FIG. 3A, the endplate 150 (and the complementary endplate 140) may comprise ramped surface 153 upon which ramped surface 136 of the distal head portion 135 may bear as the implant 10 is expanded. The ramp 136/153 mechanism may cooperate with the lateral post 137 and track 155 system in order to optimize the opening and/or expansion of the implant 10. For example, the ramp 136/153 mechanism may provide a leading expansion mechanism that is subsequently assisted by the lateral post 137 and track 155 system to expand the implant as the plug 130 is moved. Furthermore, the lateral post 137 and track 155 system may also render the expansion of the implant 10 reversible by pulling the endplates 140,150 inward towards the frame 100 along a relatively smooth ramped incline provided by the ramp 136/153 mechanism. Furthermore, the plug 130 may comprise separate connecting elements 132, 133 such that the distal head portion 135 of the plug may be distally movable relative to the frame 100 without rotation while a proximal portion of the plug 130 (such as that portion defining the threaded outer surface 131) is able to freely rotate in the distal aperture 121 of the distal wall 120 of the frame 100.

In other embodiments, as shown generally in FIGS. 5-8, the plug 230 may include a distal head portion 235 comprising a tapered cylinder. In some such embodiments, the distal head portion 235 may be configured to rotate with the plug 230 and/or move only distally D relative to the frame 100 as a proximal portion (defining the outer threaded surface 231, for example) is rotated relative to the frame 100 to drive the plug 230 in the distal direction D. According to some such embodiments, the distal head portion 235 may be configured to cooperate with a contoured bearing surface 253 (comprising in some instances a ramp and/or frustoconical concave surface) defined on an interior surface of the endplates 240, 250.

The distal head portions 135, 235 may be configured in various ways to provide a lead-in or gradual taper in order to allow for an easier interaction between the plug 130, 230 and the endplates 140, 150 or 240, 250. For example, as shown generally in the partially disassembled view of FIG. 3 (where the first endplate 140, is removed), the distal head portion 135 comprises a ramp 136 or wedge suitable for urging a complementary ramped or contoured surface 153 on the inside of the endplates 140, 150 (see FIG. 3A, showing an isolated view of one endplate 150 with an exemplary ramp 153 formed therein) so as to gradually move the endplate 140 away from the frame 100 as the plug 130 is advanced distally along the length L of the implant 10. Similarly, in the embodiments shown in FIGS. 5-8, the distal head portion 235 may be tapered to provide a lead-in or frustoconical shape that may be optimized with a taper that allows for a mechanical advantage to be realized when urging the endplates 240, 250 away from the frame 200. The resulting open configuration of the implant 20 is shown, for example, in FIG. 6. Furthermore, it should be understood that a variety of ramp and/or taper configurations may be used to optimize the interaction of the plug 130, 230 with the endplates 140, 150 or 240, 250. Such configurations may include, but are not limited to: sequential ramps or tapered frustoconical surfaces with varying angles; shallow angle sequential ramps or tapered frustoconical surfaces leading into higher angle sequential ramps or tapered frustoconical surfaces (increasing the mechanical advantage once an initial expansion of the implant 10 has been achieved), as well as other opening mechanisms (such as the lateral post 137 and track 155 system shown generally in FIGS. 2-4 that may combine to assist the ramps 136 (and 153, See FIG. 3A) in expanding the implant 20).

As shown in FIGS. 2-4, in some embodiments of the expandable spinal implant 10, the distal head portion 135 may comprise a lateral post 137 extending from the distal head portion 135 of the plug 130 and configured for cooperating with a corresponding channel 145, 155 defined in the endplates 140, 150. The channels may be angled or partially angled to provide additional mechanisms for assisting in the expansion of the implant 10 as the plug 130 is advanced distally along the length L of the implant 10. Referring more particularly, to FIG. 2, the first endplate 140 may define at least one lateral channel 145 configured to receive the lateral post 137 such that when the plug 130 is moved in a distal direction along the length L, the lateral post 137 of the distal head portion 135 is moved in a first direction in the lateral channel 145 to expand the first endplate 140 outward from the frame 100. The post 131 and channel 145 mechanism may also aid in making the implant 10 expansion substantially reversible such that when the plug 130 is moved in a proximal direction (i.e. towards the distal wall 110 of the frame 100) the lateral post 137 of the distal head portion 135 is moved in a second direction in the lateral channel 145 to contract the first endplate 140 towards the frame 100 (which may result in the implant 10 returning to the closed or unexpanded configuration shown generally in FIG. 1). This reversible feature, combined with the threaded mechanism of the plug 130 renders the implant 10 capable of being incrementally expanded or contracted through a substantially infinitely adjustable range of motion (bounded only by the length of the plug 130 and the corresponding bearing surfaces (see 253, FIG. 6, for example) defined by the endplates of the implant 10)).

Figure 9:
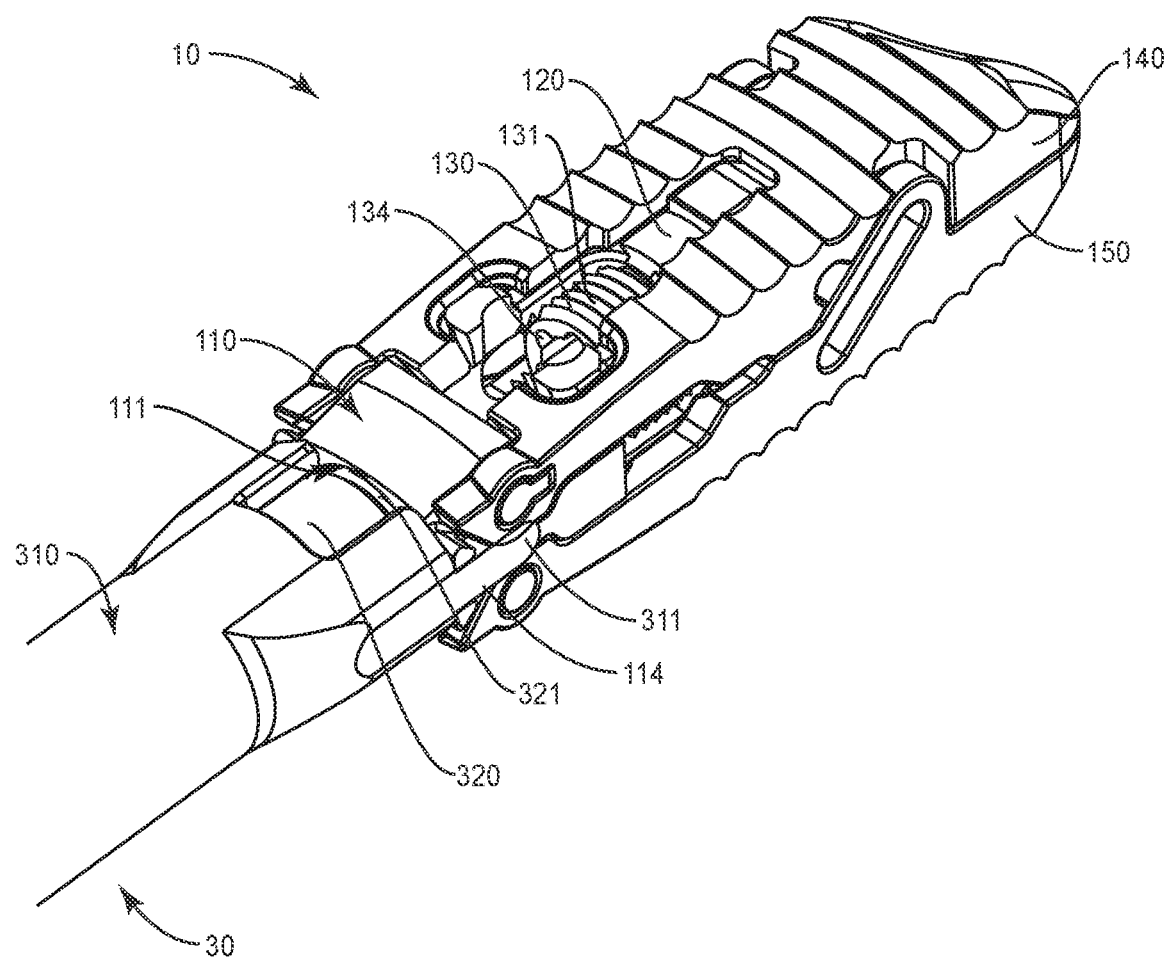
FIG. 9 is a perspective view of the components of an expandable spinal implant system including an insertion instrument engaged with an expandable spinal implant in accordance with the principles of the present disclosure.
Figure 17:
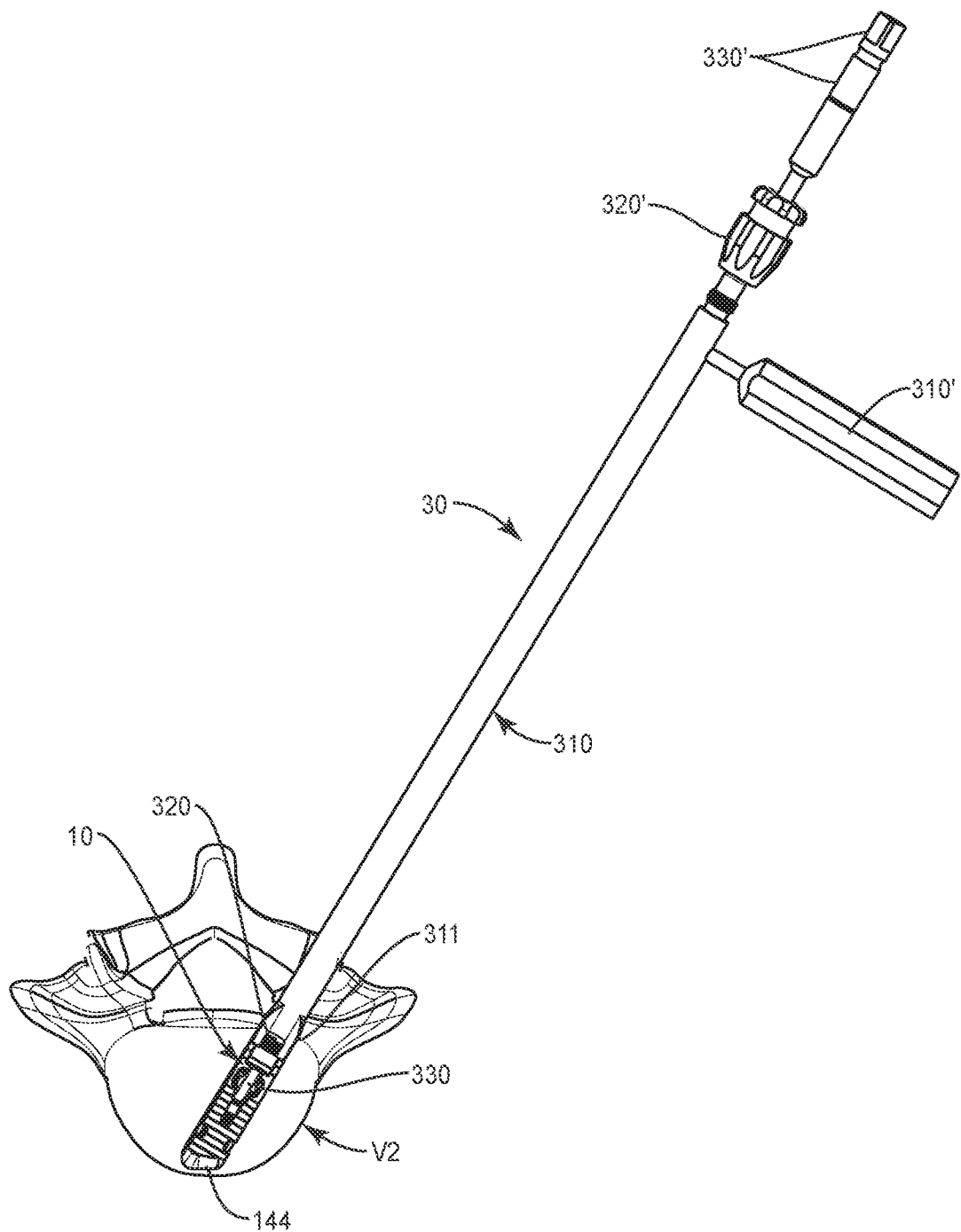
FIG. 17 is a perspective view of the components shown in FIG. 15 as used in a TLIF surgical procedure in accordance with the principles of the present disclosure.

In some embodiments, the expandable spinal implant system 10, 20 may be configured to be operable with and/or inserted by an insertion instrument 30 (see generally FIG. 17 for example). In some such embodiments, as shown in FIG. 9, the expandable spinal implant 10 may comprise a frame 100 comprising a proximal wall 110 and a distal wall 120. The proximal wall 110 may further define a proximal aperture 111 and the distal wall 110 may further define a distal aperture 121. As described herein, one or both of the proximal aperture 111 and the distal apertures 121 may be internally threaded to receive other threaded components. In some embodiments, the proximal wall 110 may be adapted to receive an insertion instrument 30 (or in some cases an inner cannula 320 of the insertion instrument 30 as shown in FIG. 9).

As described herein, the expandable spinal implant 10 may also comprise a plug 130 movably disposed in the distal aperture 121, wherein the plug 130 comprises an interface 134 adapted to be operably engaged by at least a portion of the insertion instrument 30 to move the plug 130. For example, in some embodiments, the insertion instrument 30 may comprise a driver shaft 330 with a driver on a distal end thereof (such as a hexalobular driver tip). The distal end of the driver shaft 330 may be engaged with the interface 134 of the plug 130 to rotate the plug in the distal aperture 121 of the frame 100 in order to expand the implant 10. As described herein, expansion of the implant 10 may be achieved by the moving the endplates 140, 150 that are operably engaged by the frame 100 and configured to move relative to the frame 100 when the plug 130 is moved by the insertion instrument 30 (or the driver shaft 330 thereof).

As shown generally in FIG. 17, the driver shaft 330 may be coaxially disposed inside an inner cannula 320 of the insertion instrument 30. Furthermore, both the driver shaft 330 and the inner cannula 320 may be coaxially disposed inside a cannula 330 of the insertion instrument 30. Each of the driver shaft 330, inner cannula 320 and cannula 310 may further be provided with various manipulation components 330', 320' and 310' respectively, so that the various components of the insertion instrument 30 may be operated and/or selectively manipulated independent of one another to perform various functions relative to the implant 10 (as described further herein).

Figure 7:
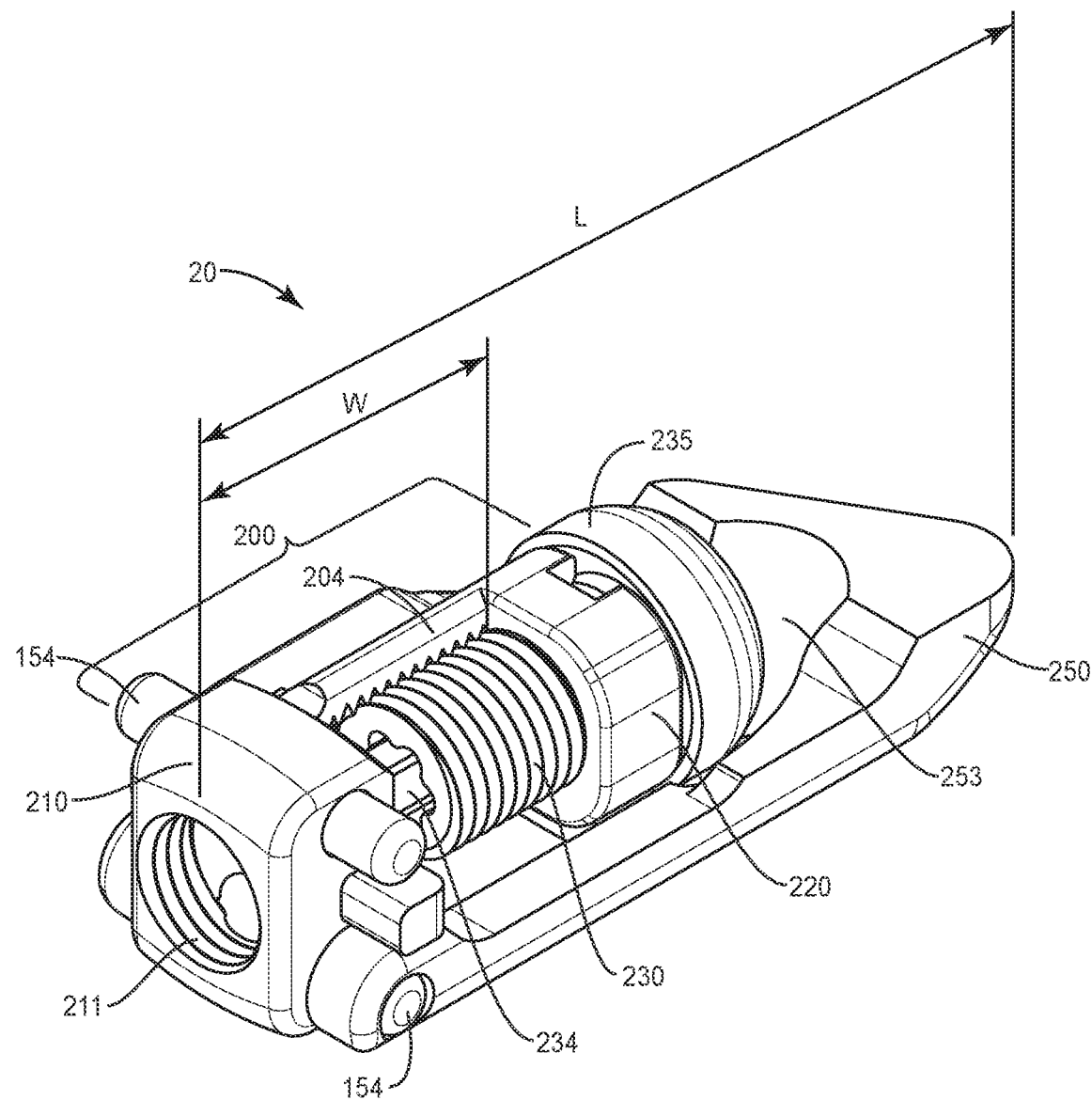
FIG. 7 is a perspective view of the components shown in FIG. 5 but with one endplate removed to show inner structures of a closed expandable spinal implant system in accordance with the principles of the present disclosure.

As described herein and shown in the embodiments of FIGS. 3 and 7, the frame 100, 200 may further comprise at least one side wall 104, 204 engaged with the proximal wall 110 and the distal wall 120 of the frame 100. The side wall 104, 204 may be configured to space the proximal wall 110 and the distal wall 120 of the frame 100 along a longitudinal axis (extending parallel to the length L) of the implant 10, 20. In some embodiments, as shown in FIG. 3, the frame 100 comprises a pair of side walls 102, 104 spaced laterally apart and engaged with the proximal wall 110 and the distal wall 120 of the frame 100 to form a substantially closed area adapted to receive and/or contain a bone growth promoting material that may be placed through the proximal aperture 111 of the frame 100. In some embodiments, the cannula 310 or inner cannula 320 of the insertion instrument 30 may be configured to convey bone growth promoting material through the insertion instrument 30 and into the area defined by the frame 100 when the implant 10 is in the expanded position (see FIG. 2, for example, showing the plug 130 moved distally forward and out of the proximal area of the implant 10 defined by the frame 100).

In some embodiments the frame 100 may be substantially "closed" with sidewalls as shown generally in FIGS. 9-12. In other embodiments, the frame 100 may comprise a pair of sidewalls 102, 104 with lateral apertures as shown generally in FIGS. 1-4. In other embodiments, as shown generally in FIGS. 5-8, the frame 200 may comprise a unilateral or single side wall 204 forming a frame 200 with one "open" lateral side. In some such embodiments as shown in FIG. 8, the frame 200 may be adapted to an least partially contain a bone growth promoting material BG that may be placed through the proximal aperture 211 of the frame 200 and/or direct the bone growth promoting material BG outside of the expandable spinal implant 20 in a lateral direction between the proximal wall 210 and the distal wall 220 of the frame 200.

FIGS. 9-12 show various configurations of an implant 10 embodiment in use with an insertion instrument 30 to form an expandable spinal implant system according to one embodiment. As shown generally in FIG. 9, the system may comprise an insertion instrument 30 comprising a cannula 310 (which may include an inner cannula 320 and an outer cannula 310 as described herein) and a driver shaft 330 (see FIG. 10 and FIG. 17) removably and rotatably disposed within the cannula 310. The system may also further comprise an expandable spinal implant 10 configured to be operably engaged with the insertion instrument 30 using a variety of mechanisms. As described herein, the implant 10 comprises a frame 100 comprising a proximal wall 110 and distal wall 120, wherein the proximal wall 110 defines a proximal aperture 111 and the distal wall 120 defines a distal aperture. The proximal wall 110 may be configured to receive a distal end of the cannula 310 (or the middle cannula 320) for manipulating the expandable spinal implant 10. For example, as shown in FIG. 9, the cannula 310 may comprise prongs 311 configured for insertion into complementary receptacles 114 defined by the proximal wall 110 of the frame 100. In other embodiments, the prongs 311 may interact with tabs or slots defined by the endplates 140, 150. The prongs 311 may interact with the receptacles 114 to enable a surgeon to manipulate the implant 10 effectively as it is engaged with a distal end of the insertion instrument. Furthermore, in some embodiments, the inner cannula 320 may comprise a threaded tip 321 configured for operably engaging threaded inner surface of the proximal aperture 111 of the frame 100. In some such embodiments, the prongs 311 of the outer cannula may serve as an effective counter-torque device (preventing rotation of the implant 10 relative to the insertion instrument 30) as the inner cannula 320 is rotated to engage the proximal aperture 111 of the frame 100. FIG. 17 shows the insertion instrument 30 in relation to the implant 10 including manipulation components 330', 320' and 310' of the insertion instrument. For example, handle 310' of the outer cannula 310 may be used to stabilize and/or manipulate the implant 10 even as the knob 320' of the inner cannula 320 is rotated within the outer cannula 310 such that the threaded tip 321 may be engaged with the proximal aperture 111 of the frame 100 without rotating the implant 100.

As described herein, the implant 10 may be configured for expansion by virtue of a plug 130 movably disposed in the distal aperture 120 of the frame 100. In some embodiments, the plug comprises a threaded outer surface 131 configured to be engaged with a complementary inner threaded surface of the distal aperture 120. In some embodiments, as shown in FIG. 9, the plug 130 may comprise an interface 134 configured to be operably engaged by a distal end of a driver shaft 330 to move (by threaded rotation, for example) the plug 130 relative to the frame. The driver shaft 330 may be coaxially placed within the cannula 310 and/or the inner cannula 310 and rotatable therein using the driver proximal end 330' of the driver shaft 330. The driver proximal end 330' may comprise a keyed or faceted surface configured for engagement with a quick-release handle (not shown) or a powered driver (not shown) for rotating the driver shaft 330. Furthermore, the plug interface 134 may comprise a drive receptacle configured to cooperate with a distal end of the driver shaft. The drive connection between the driver shaft 330 and the plug interface 134 may comprise a variety of drive interfaces including but not limited to: multi-lobular drives; hexalobular drives; cross or Phillips head drives; straight or "flat head" drives; square or other polygonal drives; and/or combinations thereof.

As described herein, the movement of the plug 130 facilitated by the driver shaft 310 within the cannula 310 (and, in some cases the inner cannula 320) may further cause the movement of an endplate 140, 150 operably engaged with the frame 100 of the implant 10 relative to the frame 100 when the plug 130 is moved by the insertion instrument 30. Thus the insertion instrument 30 (or the driver shaft 330 and driver proximal end 330') may be used to expand the endplates 140, 150 relative to the frame 100 in order to selectively expand the implant 10 and/or impart a lordotic movement in adjacent vertebral bodies V1, V2 as shown generally in FIGS. 14 and 16. The length of the driver shaft 330 may be adjusted to account for the distal placement of the distal wall 120 of the frame 100 relative to the length L of the implant 10. For example, the driver shaft 330 may be provided with a length that substantially exceeds that of the cannula 310 and/or inner cannula 320 so that the driver proximal end 330' remains accessible and engaged with a handle or powered driver even when the driver shaft 330 remains engaged with the plug 130 of the implant 10 when the implant is in the fully expanded condition (see FIGS. 14 and 16). This feature may be important in situations where a surgeon wishes to reverse the expansion of the implant 10 as described further herein with respect to the post 131 and channel 145 mechanisms of particular implant 10 embodiments.

According to various embodiments, the driver shaft 330 may also be configured to be removable from the cannula 310 (and/or the inner cannula (if employed)), such that after the plug 130 of the implant 10 has been moved distally relative to the frame 100, a bone growth promoting material BG may be introduced into the frame 100 of the expandable spinal implant 10 through the cannula 310 (and/or through the concentric inner cannula 320, when used). The bone growth promoting material BG may be tamped or urged through the cannula 310 or inner cannula 310 using the driver shaft 330 or other tamp and/or rod (not shown) sized for slidable insertion through the cannula 310 and/or inner cannula 310. A funnel (not shown) or other attachment may also be inserted into a proximal end of the cannula 310 or inner cannula 320 (such as at the point near the proximal end or knob 320' of inner cannula 320, as shown in FIG. 17) to facilitate the introduction of the bone growth promoting material BG into the cannula 310 and/or inner cannula 320.

Figure 10:
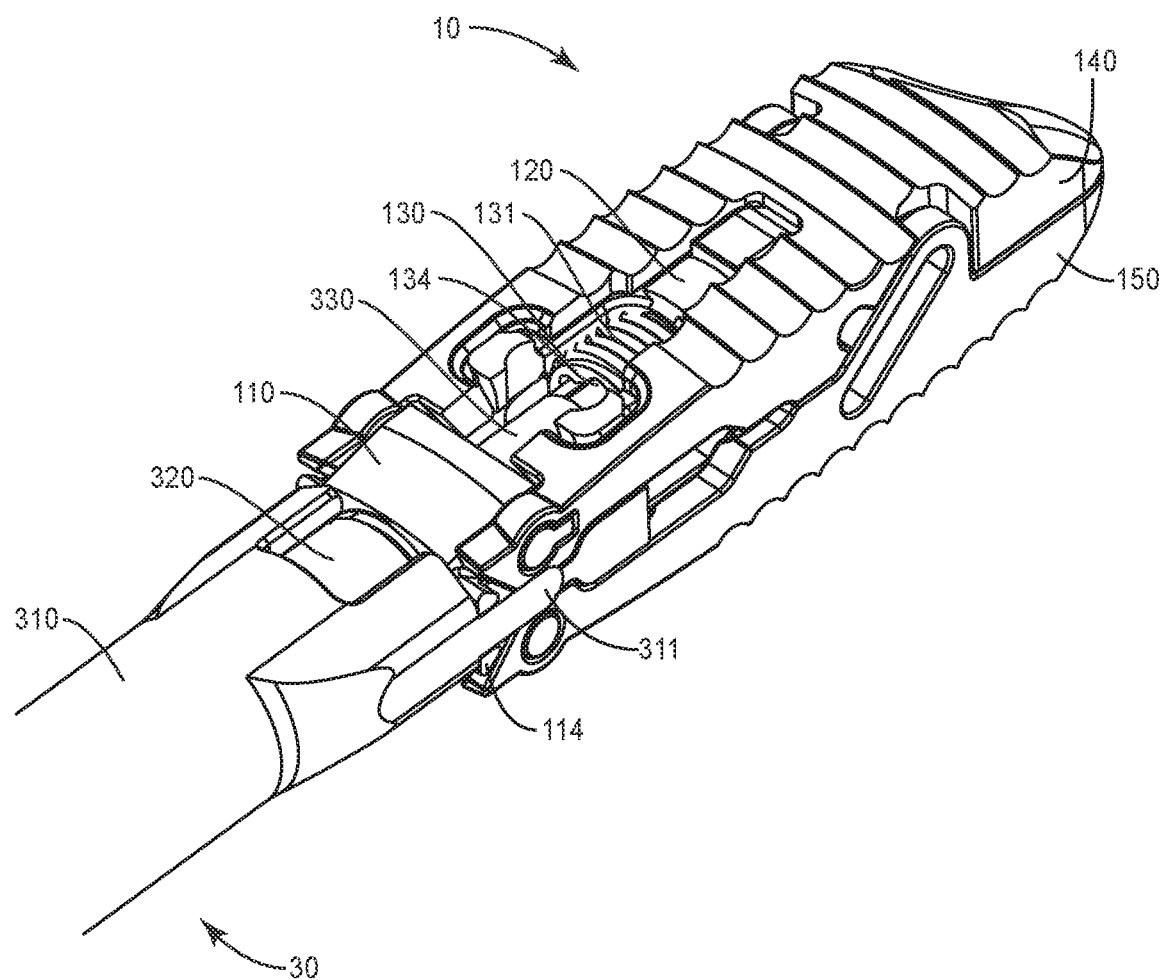
FIG. 10 is a perspective view of the components shown in FIG. 9 also showing a driver shaft extended through the cannula and in engagement with the plug.
Figure 11:
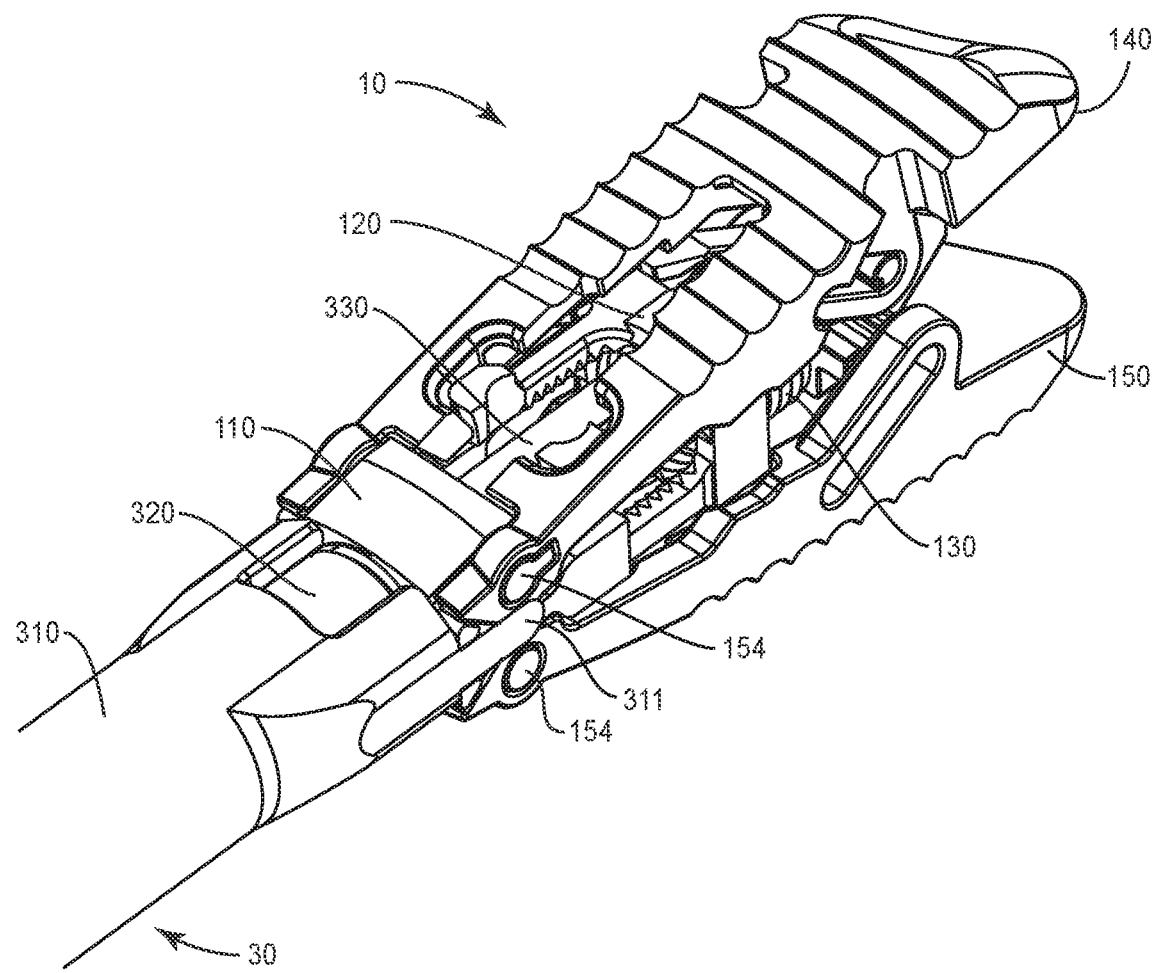
FIG. 11 is a perspective view of the components shown in FIG. 9 also showing a driver shaft extended through the cannula and in engagement with the plug to expand the endplates relative to the frame.
Figure 12:
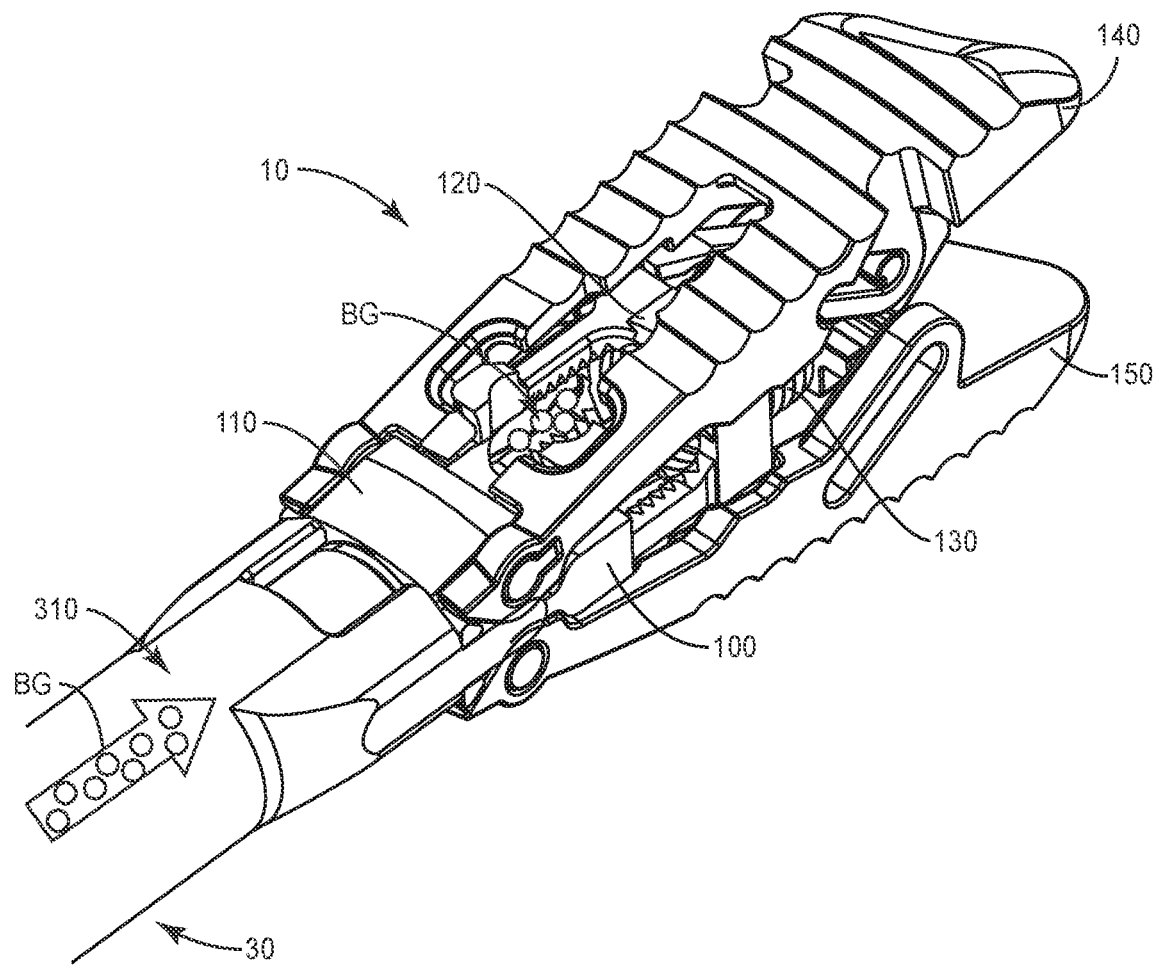
FIG. 12 is a perspective view of the components shown in FIG. 9 also showing the driver shaft removed from the cannula.

FIGS. 9-12 depict exemplary procedural steps for the use of the implant system in one embodiment. For example, FIG. 9 shows an unexpanded implant 10 attached to insertion device 30 using the prongs 311 of the cannula 310 and the distal end 321 of inner cannula 320. The plug 130 is shown engaged with the distal aperture of distal wall 120 of the frame and the plug interface 134 is visible. In FIG. 10, the driver shaft 330 is shown extended through cannula 310 and inner cannula 320 and engaged with the plug interface 134. Referring to FIG. 17, the driver proximal end 330' may be rotated at this step to drive the plug 130 forward to expand the endplates 140, 150 relative to the frame 100. FIG. 11 shows the result of the interaction of the driver shaft 330 with the plug 130 and the distal movement of the plug 130 relative to the distal wall 120 of the frame 100 to expand the endplates 140, 150 relative to the frame 100 of the implant 10. FIG. 12 shows the insertion device 30 still engaged with the implant 10 but with the driver shaft 330 removed from the cannula 310 and inner cannula 320, leaving the cannulas open for the introduction of bone growth promoting material BG through the insertion instrument 30 and into a proximal portion of the implant 10 defined generally by the now-open interior of the frame 100.

Referring to exemplary FIGS. 13-16, spinal implant system 10, 30 can be employed with a surgical arthrodesis procedure, such as, for example, an interbody fusion for treatment of an applicable condition or injury of an affected section of a spinal column and adjacent areas within a body, such as, for example, intervertebral disc space between a vertebra V1 and a vertebra V2. In some embodiments, spinal implant system 10, 30 can include an intervertebral implant that can be inserted with intervertebral disc space to space apart articular joint surfaces, provide support and maximize stabilization of vertebrae V1, V2. In some embodiments, spinal implant system 10, 30 may be employed with one or a plurality of vertebra.

Figure 13:
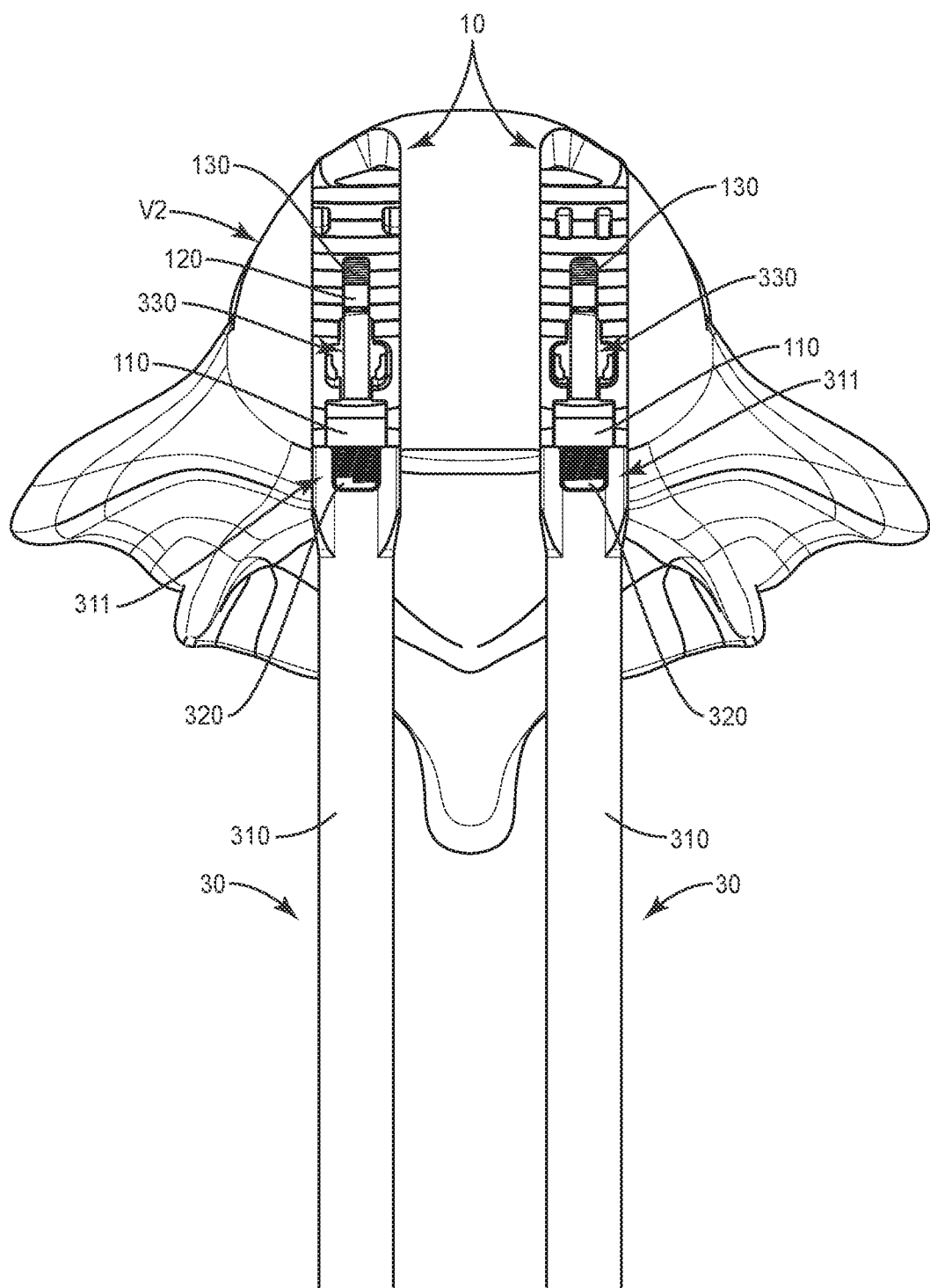
FIG. 13 is a top view of one embodiment of an expandable spinal implant system as used in a PLIF surgical procedure in accordance with the principles of the present disclosure.
Figure 15:
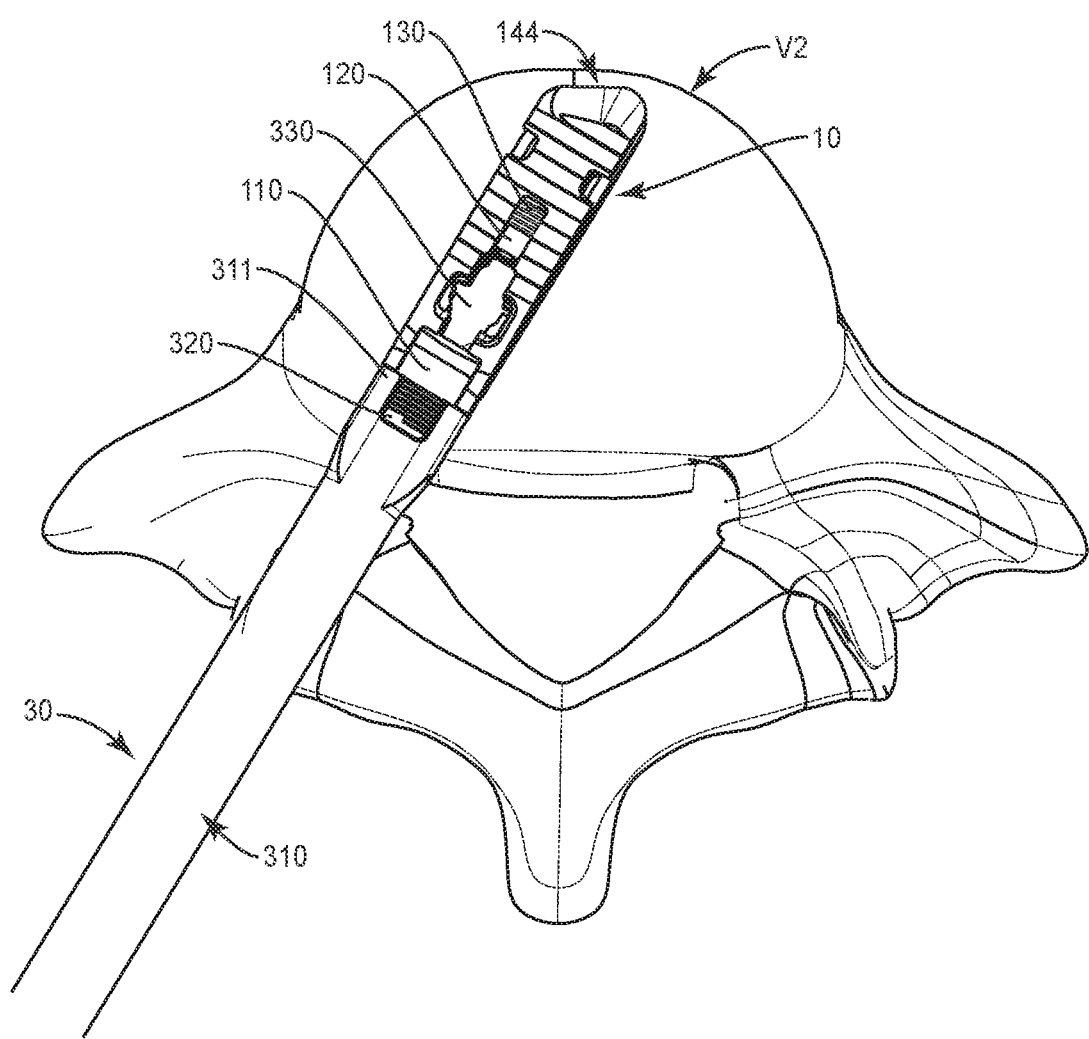
FIG. 15 is a top view of one embodiment of an expandable spinal implant system as used in a TLIF surgical procedure in accordance with the principles of the present disclosure.

A medical practitioner obtains access to a surgical site including vertebrae V1, V2 such as through incision and retraction of tissues. Spinal implant system 10, 30 can be used in any existing surgical method or technique including open surgery, mini-open surgery, minimally invasive surgery and percutaneous surgical implantation, whereby vertebrae V1, V2 are accessed through a mini-incision, retractor, tube or sleeve that provides a protected passageway to the area. In one embodiment, the components of spinal implant system 10, 30 are delivered through a surgical pathway to the surgical site along a surgical approach into intervertebral disc space between vertebrae V1, V2. Various surgical approaches and pathways may be used. FIG. 13 shows an example of a typical posterior lumbar interbody fusion (PLIF) approach using the spinal implant system 10, 30 wherein a pair of implants 10 may be delivered, expanded to impart or restore a lordotic curve (see generally FIG. 14), and then post-packed with bone growth promoting material BG after the removal of the driver shaft 330 from the insertion instrument 30. As shown in FIG. 15, unilateral approaches such as a transforaminal lumbar interbody fusion (TLIF) approach may also be used to place the implant in a substantially oblique position relative to the vertebrae V1, V2. In such procedures the distal end 144 of the endplates 140, 150 may be shaped so that the implant 10 fits within the intervertebral space defined by the extents of the vertebral body V2 as shown in FIG. 15. Furthermore, in oblique placement applications the implant 10 endplates 140, 150 may also be provided with complementary oblique contact surfaces shaped to better impart and/or restore a lordotic curve as the implant 10 is expanded as shown generally in FIG. 16. Furthermore, the endplates 140, 150 of the implant may be provided with a variety of ridges, teeth, coatings or other surface treatments suitable for interacting with and/or securing relative to the adjacent vertebrae V1, V2.

As will be appreciated by one of skill in the art, a preparation instrument (not shown) may be employed to remove disc tissue, fluids, adjacent tissues and/or bone, and scrape and/or remove tissue from endplate surfaces of vertebra V1 and/or endplate surface of vertebra V2 in preparation for the procedures utilizing the system 10, 30. In some embodiments, the size of implant 10 is selected after trialing using trialing instruments (not shown) that may approximate the size and configuration of the system 10, 30 (as shown in FIG. 17, for example). In some embodiments, such trials may be fixed in size and/or be fitted with expansion mechanisms similar to the various implant 10, 20 embodiments described herein. In some embodiments, implant 10 may be visualized by fluoroscopy and oriented before introduction into intervertebral disc space. Furthermore, the insertion instrument 30 and implant 10 may be fitted with fiducial markers to enable image guided surgical navigation to be used prior to and/or during a procedure.

In some embodiments as shown generally in FIGS. 13 and 15, implant 10 provides a footprint that improves stability and decreases the risk of subsidence into tissue. In some embodiments as shown generally in FIGS. 14 and 16, implant 10 provides angular correction, height restoration between vertebral bodies, decompression, restoration of sagittal and/or coronal balance and/or resistance of subsidence into vertebral endplates. In some embodiments, implant 10 engages and spaces apart opposing endplate surfaces of vertebrae V1, V2 and is secured within a vertebral space to stabilize and immobilize portions of vertebrae V1, V2 in connection with bone growth for fusion and fixation of vertebrae V1, V2.

Components of spinal implant system 10, 30 including implant 10 can be delivered or implanted as a pre-assembled device or can be assembled in situ. Components of spinal implant system 10, 30 including implant 10 may be expanded, contracted, completely or partially revised, removed or replaced in situ. In some embodiments, one or all of the components of spinal implant system 10, 30 can be delivered to the surgical site via mechanical manipulation and/or a free hand technique.

In one embodiment, spinal implant system 10, 30 includes a plurality of implants 10 (see FIG. 13 for one example). In some embodiments, employing a plurality of implants 10 can optimize angular correction and/or height restoration between vertebrae V1, V2 The plurality of implants 10 can be oriented in a side by side engagement, spaced apart and/or staggered.

In some embodiments, spinal implant system 10, 30 includes an agent, including but not limited to the bone growth promoting materials BG described herein, which may be disposed, packed, coated or layered within, on or about the components and/or surfaces of spinal implant system 10, 30. In some embodiments, the agent may include bone growth promoting material to enhance fixation of implant 10 with bony structures. In some embodiments, the agent may include one or a plurality of therapeutic agents and/or pharmacological agents for release, including sustained release, to treat, for example, pain, inflammation and degeneration.

In one embodiment, implants 10, 20 may include fastening elements, which may include locking structure, configured for fixation with vertebrae V1, V2 to secure joint surfaces and provide complementary stabilization and immobilization to a vertebral region. In some embodiments, locking structure may include fastening elements, such as, for example, rods, plates, clips, hooks, adhesives and/or flanges. In some embodiments, the components of spinal implant system 10, 30 can be used with screws to enhance fixation. The components of spinal implant system 10 can be made of radiolucent materials such as polymers. Radiopaque markers may be included for identification under x-ray, fluoroscopy, CT or other imaging techniques. The insertion instrument 30 alone or with the tube for insertion therethrough described above may be radiolucent and may optionally include markers added at the distal tip and/or along the length of one or both of insertion instrument 30 and the tube to permit them to be seen on fluoroscopy/x-ray while advancing into the patient. If the implant 10 includes radiolucent markers placed near the proximal end this may permit visualization of the proximity of the tip of the tube moving toward the proximal end of the implant 10.

In one embodiment of the invention, the endplates 140 and 150 include an anterior portion 400 extending to one side of the implant from one side only of respective lateral surfaces at the respective distal ends of the endplates 140 and 150. The anterior portion 400 extends along an axis 1-1, which extends transverse to the central longitudinal axis CL. Anterior portion 400 ends in an anterior tip 402. As depicted in FIGS. 19-23 and 27-32, when the implant is in the collapsed position, the anterior portion 400 and the anterior tip 402 define a distal end hooked portion 404. When the implant is in the collapsed position, the distal end of the first endplate 140 combines with the distal end of the second endplate 150 to define a distal end beveled portion 406. The distal end hooked portion 404 provides each of the endplates 140/150 with an increased surface area, enabling them to withstand greater loads during implant expansion, and to create lordosis.

Figure 23:
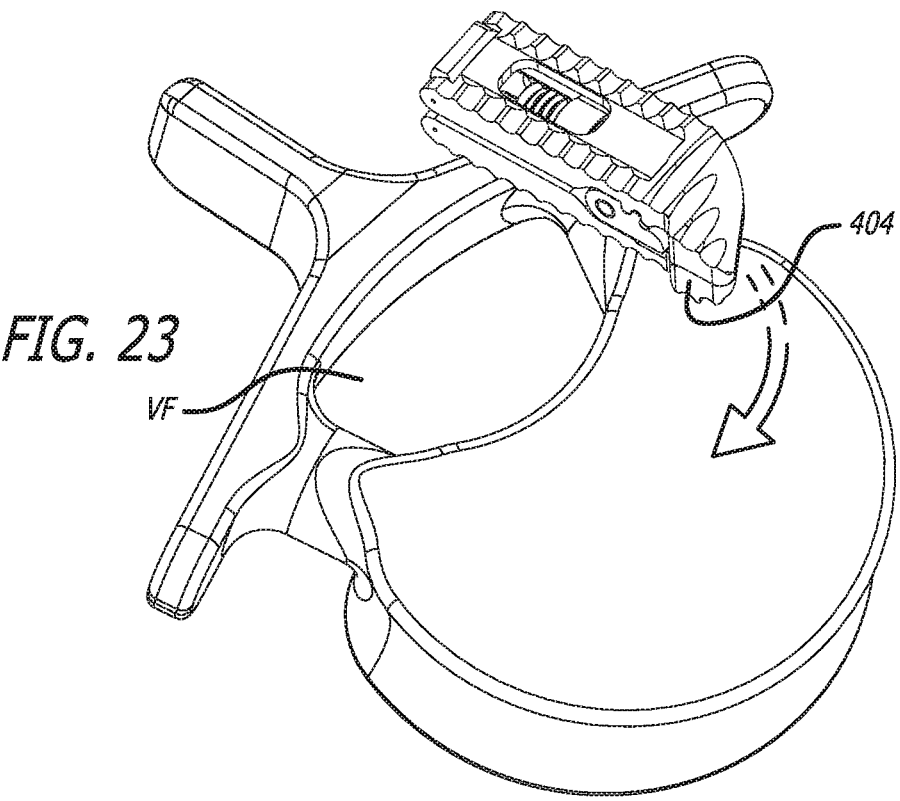
FIG. 23 is a perspective view depicting an insertion path into a disc space of one embodiment of an expandable spinal implant having an anterior projection and an anterior tip defining a distal end hook portion hooking around a vertebral foramen of a vertebral body.
Figure 35:
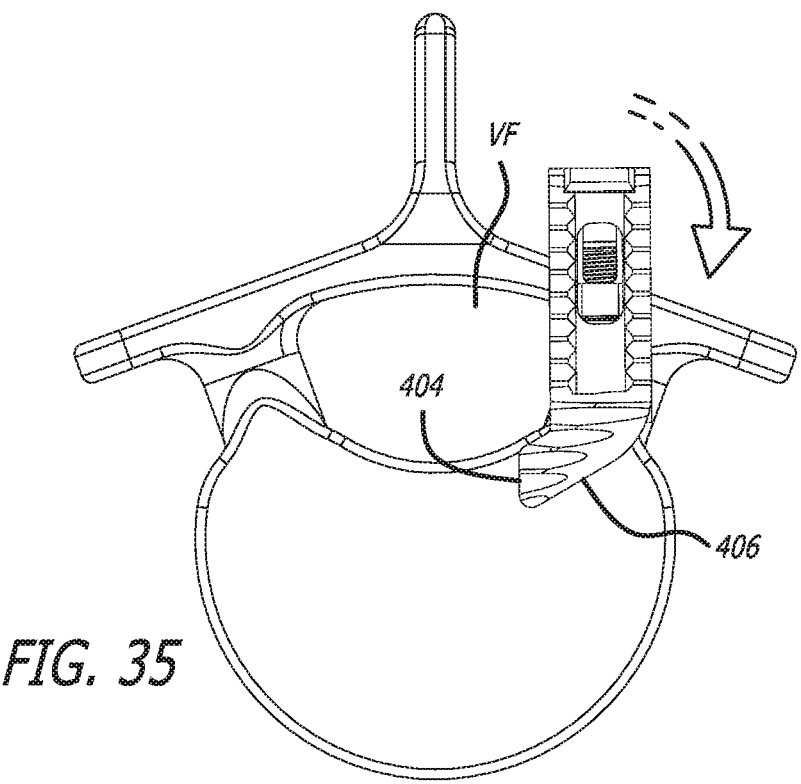
FIG. 35 is an upper view of one embodiment of an expandable spinal implant having an anterior projection and an anterior tip defining a distal end hook portion being inserted into a disc space, with the distal end hook portion hooking around the vertebral foramen, thereby avoiding contact with at least the spinal cord.

In one embodiment of the invention, at least the distal end hooked portion 404 is configured, as depicted in FIGS. 23 and 35, upon insertion of the implant 10 into a disc space between an upper vertebral body and a lower vertebral body, to hook around the vertebral foramen VF, thereby avoiding interference with the neural elements, particularly the spinal cord, located in the vertebral foramen.

Figure 36:
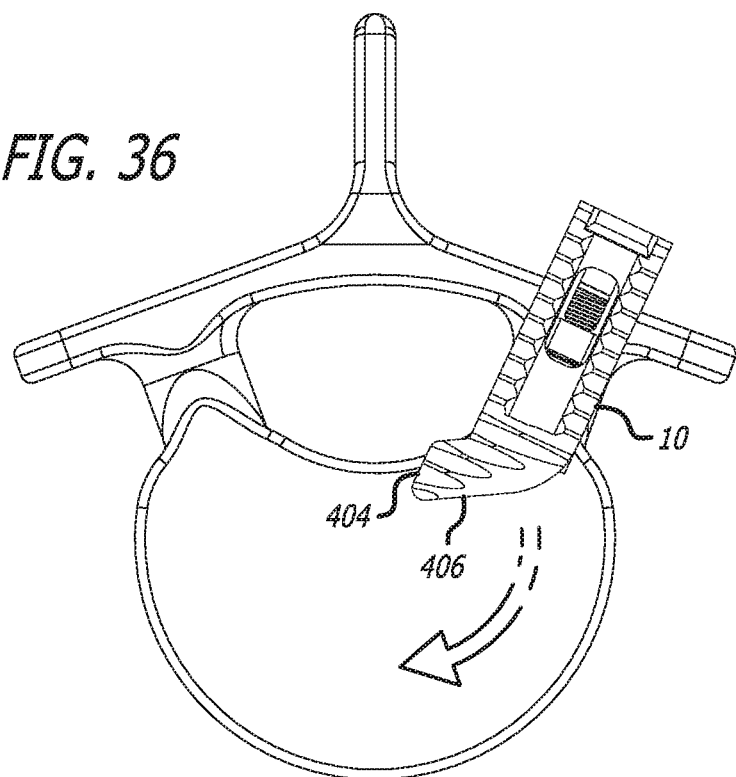
FIG. 36 is an upper view of one embodiment of an expandable spinal implant having an anterior projection and an anterior tip defining a distal end being inserted into a disc space, with the distal end hook portion rotating to a TLIF/transverse pathway.

In one embodiment of the invention, at least the distal end hooked portion 404 is further configured, as depicted in FIG. 36, upon insertion of the implant into the disc space, to rotate from a laterally divergent pathway to a TLIF/transverse pathway.

Figure 24:
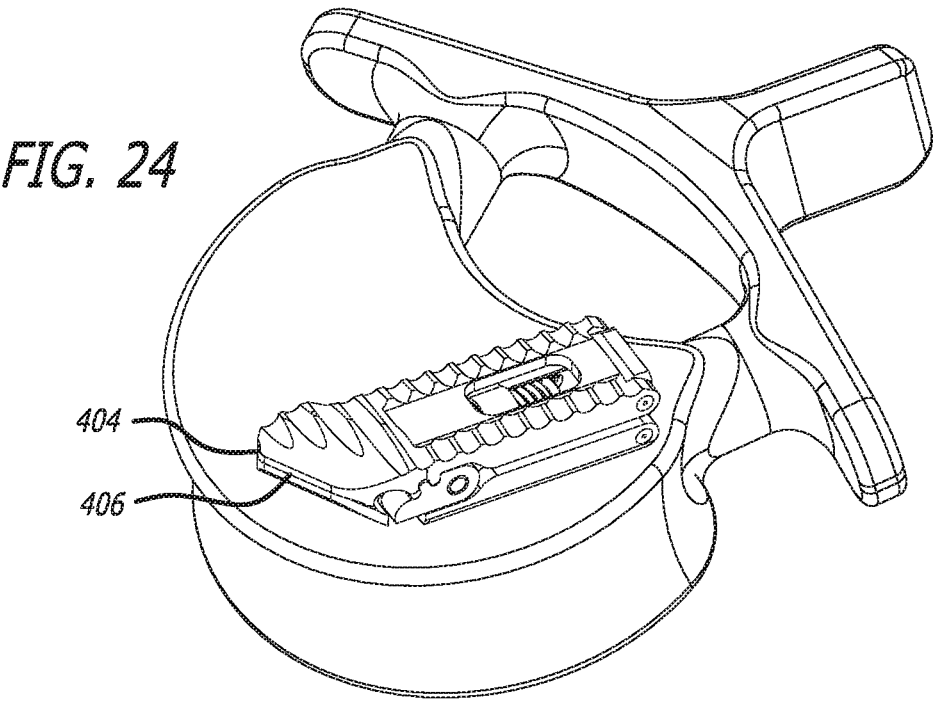
FIG. 24 is a perspective view depicting a continued insertion path into a disc space toward an anterior apophyseal rim of a vertebral body of one embodiment of an expandable spinal implant having an anterior projection and an anterior tip defining a distal end hook portion.
Figure 25:
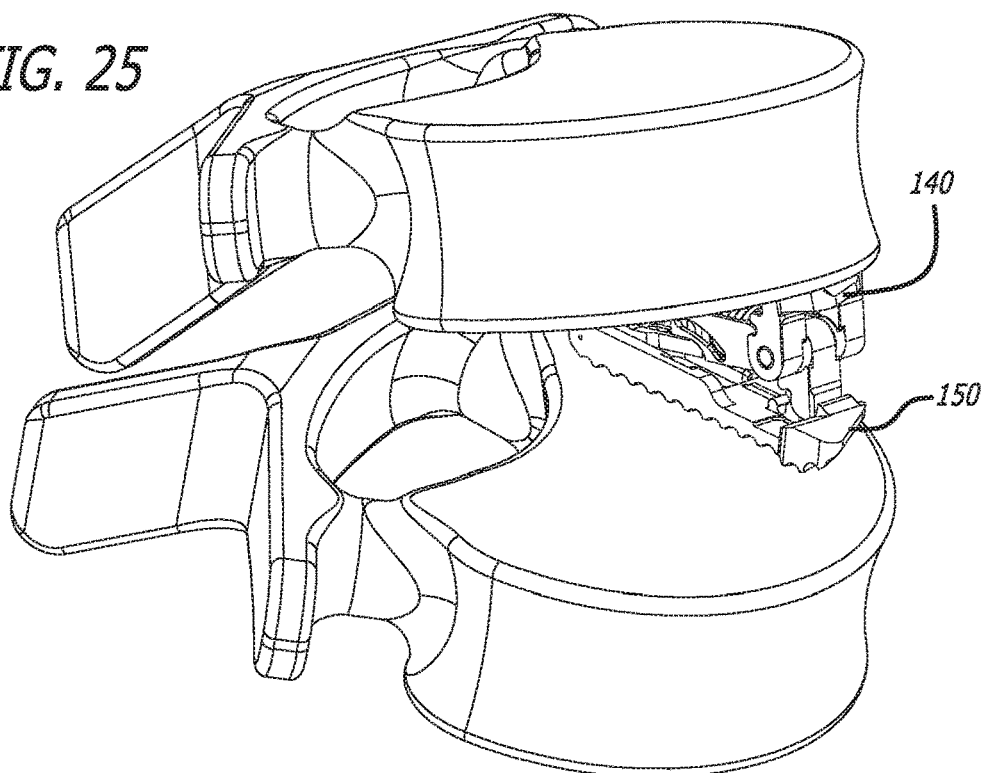
FIG. 25 is a perspective view depicting one embodiment of an expandable spinal implant having an anterior projection and an anterior tip defining a distal end hook portion, positioned between upper and lower vertebral bodies, expanding toward an expanded position.
Figure 26:
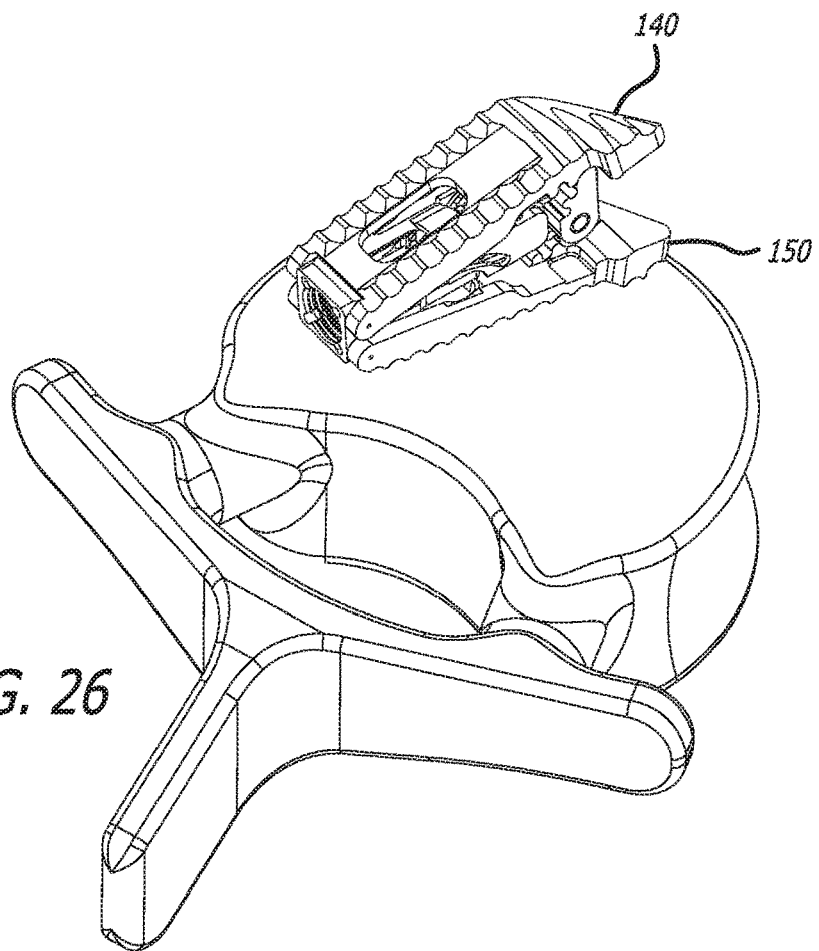
FIG. 26 is a perspective view depicting one embodiment of an expandable spinal implant having an anterior projection and an anterior tip defining a distal end hook portion positioned on a lower vertebral body, expanding toward an expanded position.
Figure 27:
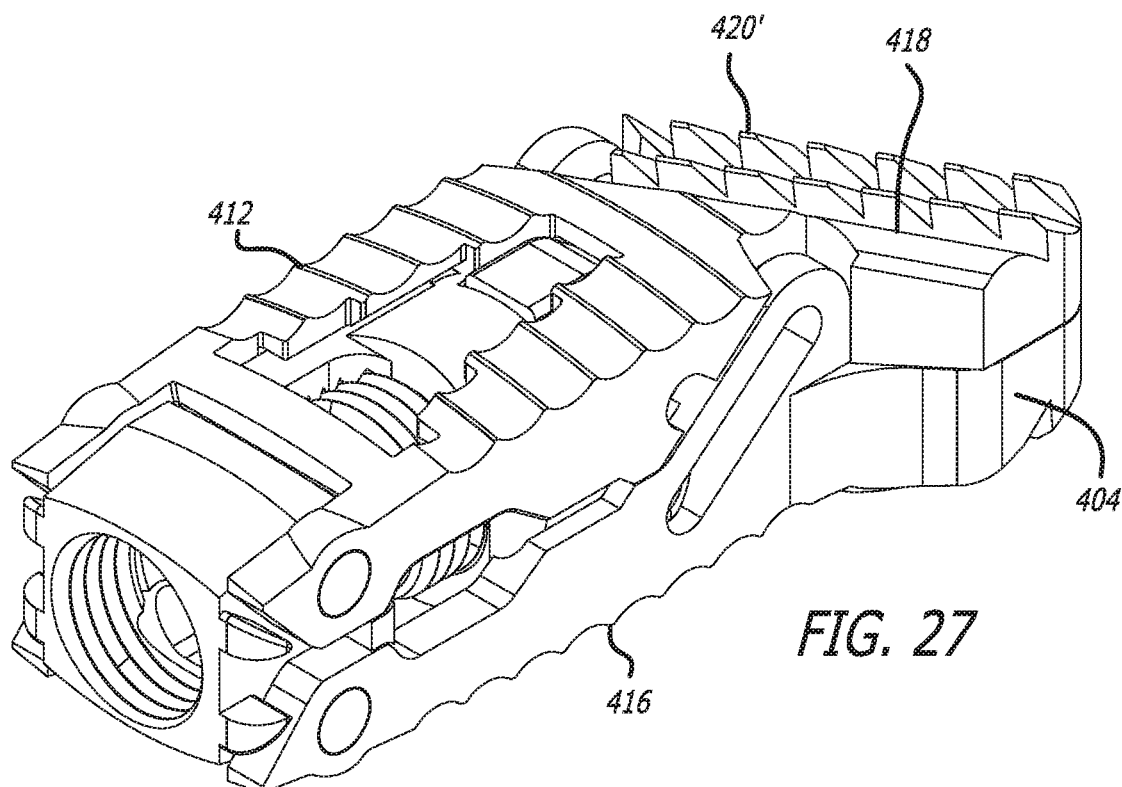
FIG. 27 is a perspective view of one embodiment of an expandable spinal implant, in a collapsed position, having an anterior projection and an anterior tip defining a distal end hook portion, including backout-prevention portions defined on the upper endplate.
Figure 28:
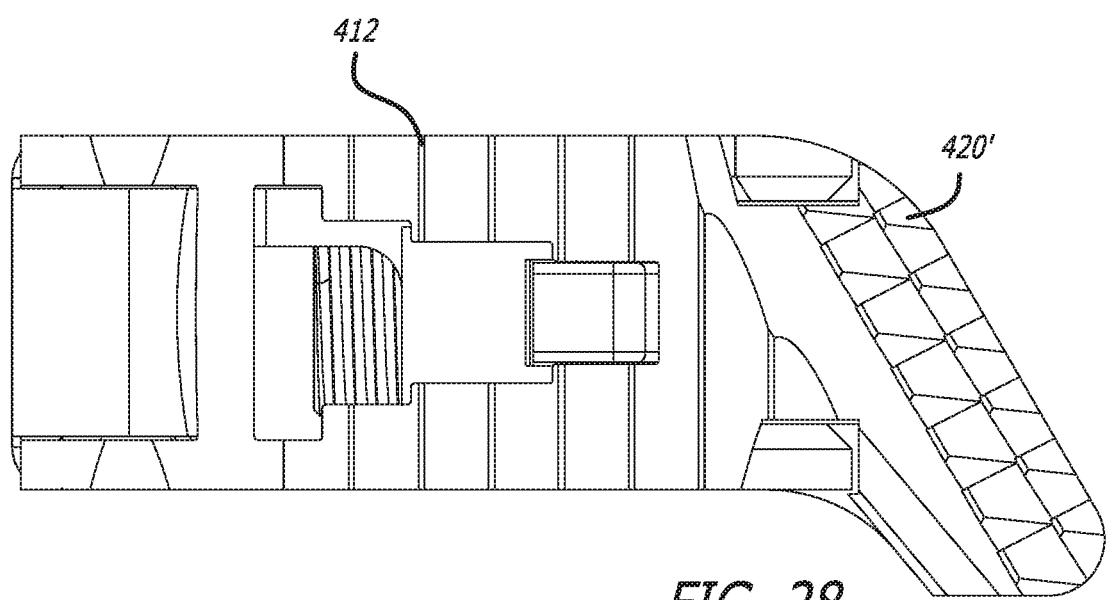
FIG. 28 is an upper view of one embodiment of an expandable spinal implant, in a collapsed position, having an anterior projection and an anterior tip defining a distal end hook portion, including backout-prevention portions defined on the upper endplate.
Figure 33:
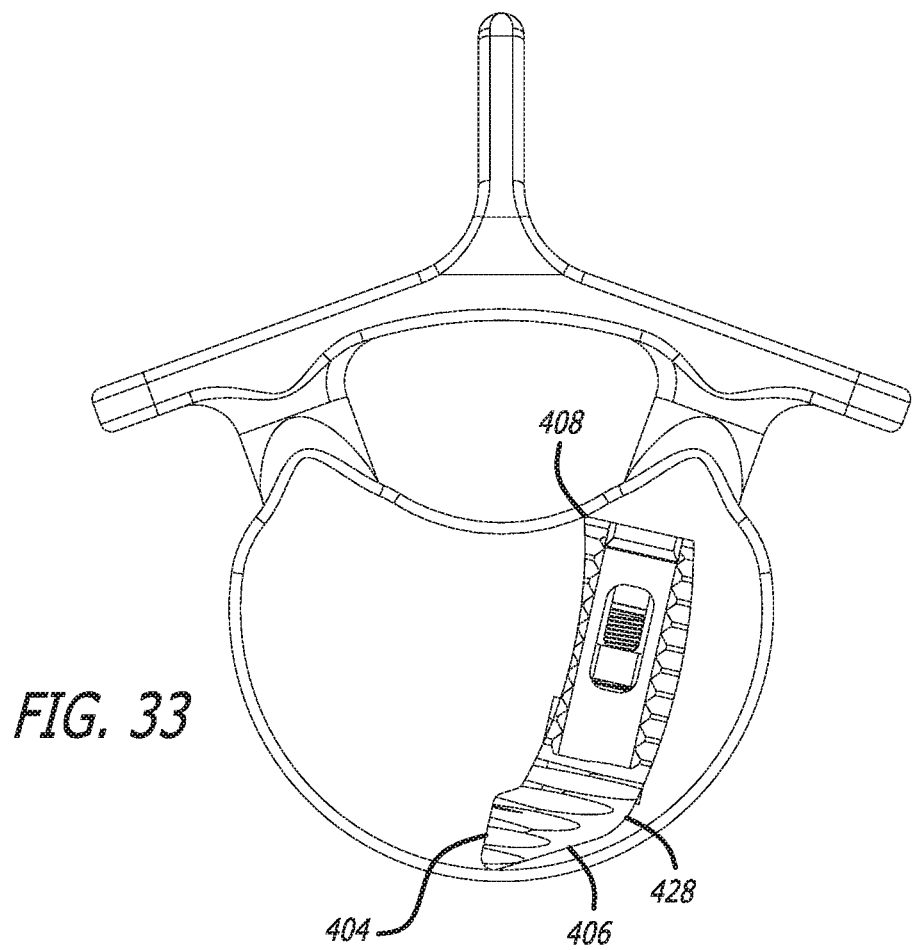
FIG. 33 is an upper view of one embodiment of an expandable spinal implant having an anterior projection and an anterior tip defining a distal end hook portion inserted into a disc space with the distal end hook portion proximate the anterior apophyseal rim, and a proximal end of the implant proximate the vertebral foramen.
Figure 34:
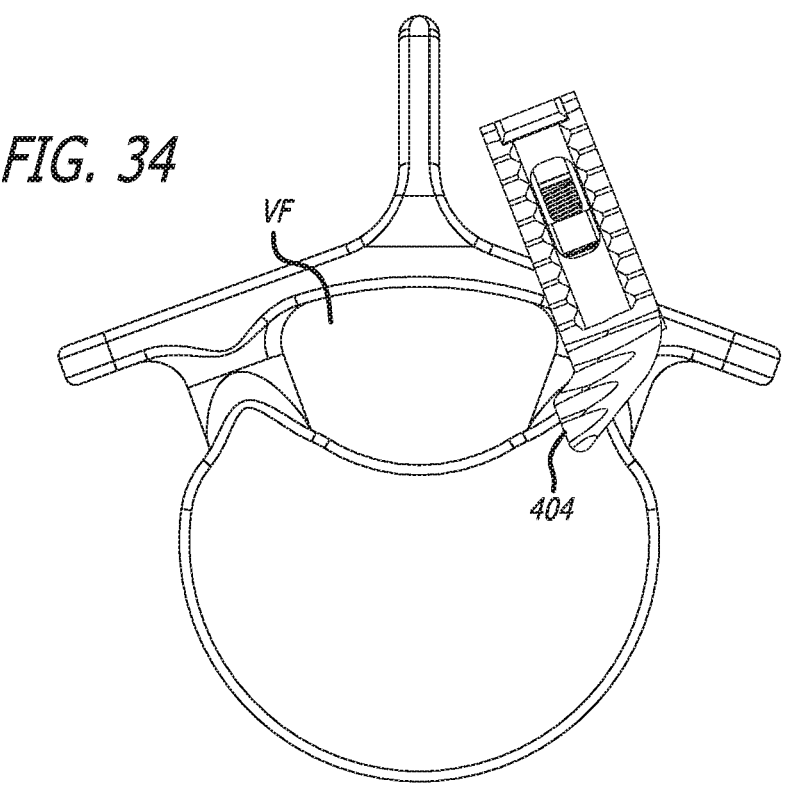
FIG. 34 is an upper view of one embodiment of an expandable spinal implant having an anterior projection and an anterior tip defining a distal end hook portion being inserted into a disc space.

In one embodiment of the invention, as depicted in FIGS. 24-26, the implant 10 is configured to be inserted into the disc space until the distal end hooked portion 404 and the distal end beveled portion 406 engage an entire portion of the anterior apophyseal rims of each of the upper and lower vertebral bodies. As depicted in FIG. 33, the distal end hook portion 404 and the distal beveled end portion 406 engage the anterior apophyseal rim, while a proximal end corner 408 contacts the posterior rim.

Figure 29:
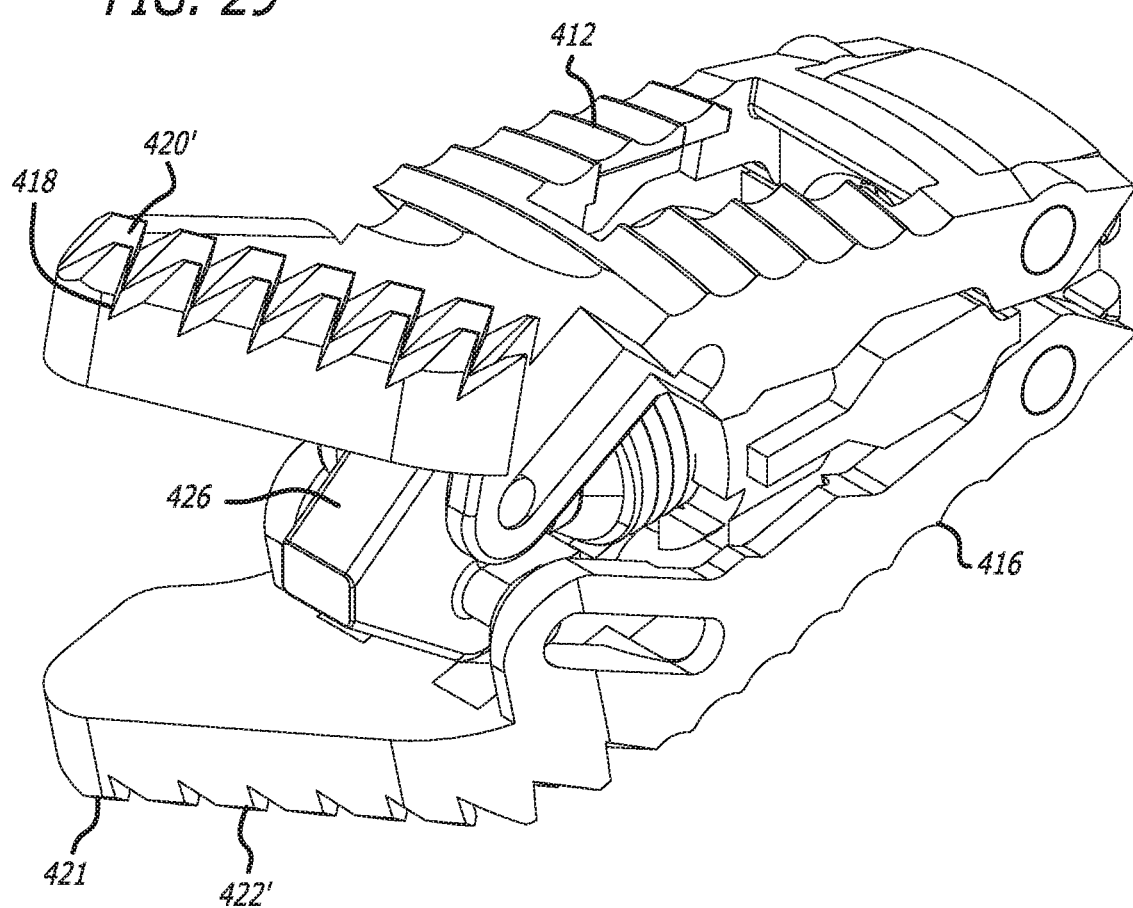
FIG. 29 is a perspective view of one embodiment of an expandable spinal implant, in an expanded position, having an anterior projection and an anterior tip defining a distal end hook portion, including backout-prevention portions defined on the upper endplate.
Figure 30:
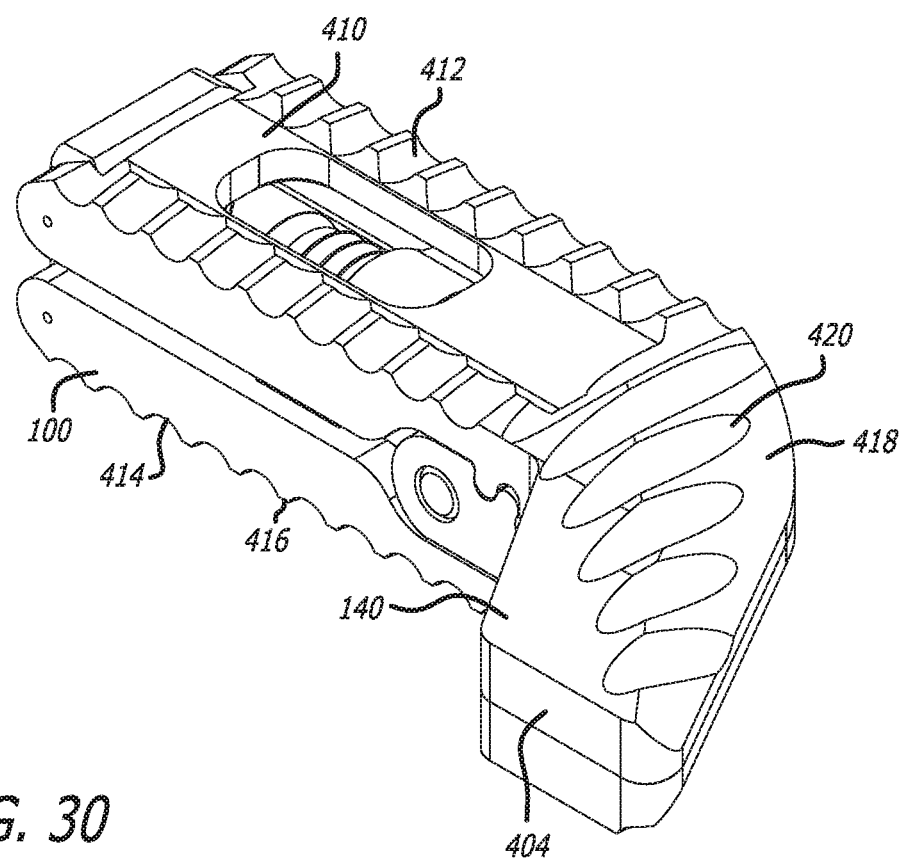
FIG. 30 is a perspective view of one embodiment of an expandable spinal implant having an anterior projection, an anterior tip defining a distal end hook portion, and an arcuate portion at the distal end opposite the distal end hook portion.

In one embodiment of the invention, as depicted in FIG. 29, the distal end hooked portion 404 and the distal end beveled portion 406 continue to engage entirely along apophyseal rims of each of the upper and lower vertebral bodies following expansion of the implant.

In one embodiment of the invention, as depicted in FIGS. 27-32, an upper surface 410 of the frame 100 includes first parallel rows of teeth 412. A lower surface 414 of the frame 100 includes second parallel rows of teeth 416. As depicted in FIGS. 27-32, at least an upper surface 418 of the first endplate 140 includes third rows of teeth 420, defined parallel to the first rows of teeth 412. Fourth rows of teeth 422 are defined at least on the lower surface 421 of second endplate 150 in an orientation parallel to the first rows of teeth 412.

In one embodiment of the invention, as depicted in FIGS. 27-32, an alternative embodiment of third rows of teeth 420' can be provided on the upper surface 418 of first endplate 140 in an orientation perpendicular to the first rows of teeth 412. Likewise an alternative embodiment of fourth rows of teeth 422' can be provided on lower surface 421 of the second endplate 150 perpendicular to the distal end beveled portion 406. Perpendicular third rows of teeth 420' and fourth rows of teeth 422' provide improved purchase against the vertebral bone of the anterior apophyseal rims when the implant 10 is in the expanded position. In addition, when the implant is in the expanded position, first rows of teeth 412, second rows of teeth 416, third rows of teeth 420, fourth rows of teeth 422, and alternate third rows of teeth 420' and fourth rows of teeth 422' all are configured to prevent inadvertent backout of the implant 10 from the anterior apophyseal rims of the upper and lower vertebral bodies. Although FIGS. 27-32 depict the respective surfaces of the endplates fully covered by the rows of teeth 420, 422, 420', and 422', it is within the scope of the invention for these rows of teeth to only partially cover the surfaces of the endplates.

Figure 31:
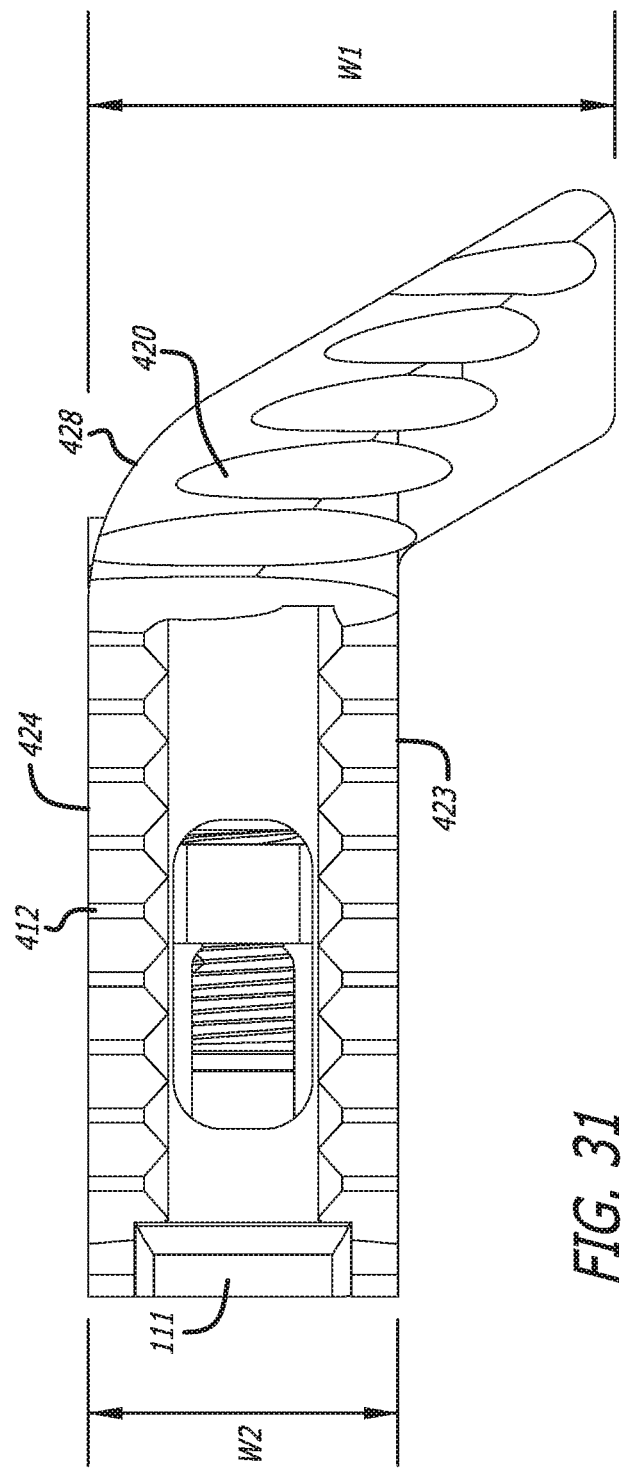
FIG. 31 is an upper view of one embodiment of an expandable spinal implant having an anterior projection and an anterior tip defining a distal end hook portion.
Figure 32:
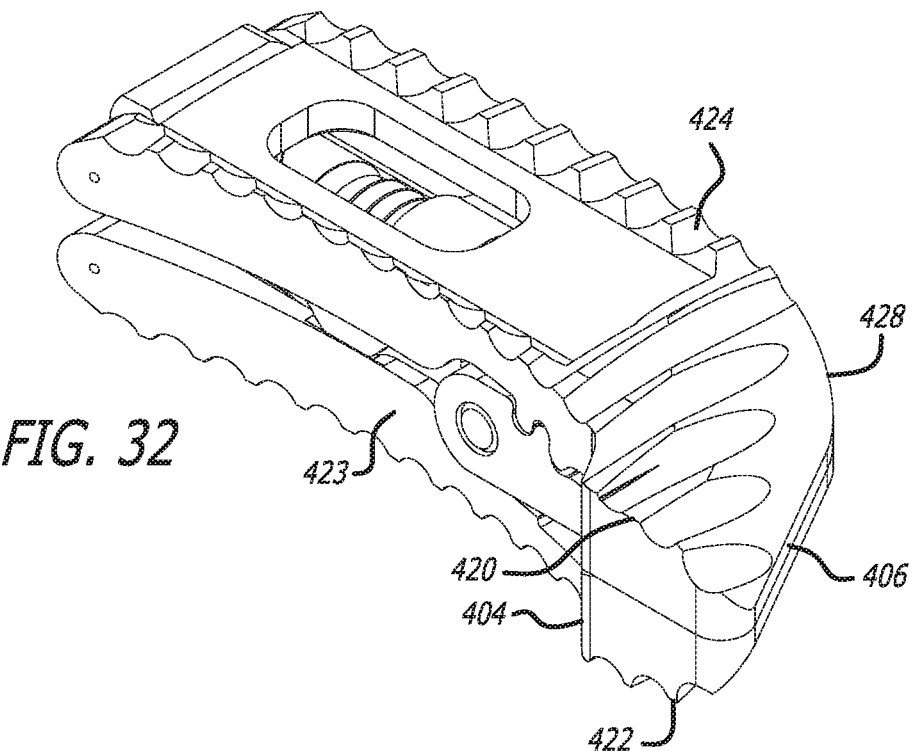
FIG. 32 is a perspective view is a perspective view of one embodiment of an expandable spinal implant having an anterior projection and an anterior tip defining a distal end hook portion.

In one embodiment of the invention, as depicted in FIG. 31, a width W1 of the implant 10 at the distal end hooked portion 404 is greater than a width W2 of the implant 10 at the frame proximal wall 110, thereby providing increased structural strength at the distal end hooked portion 404.

Figure 37:
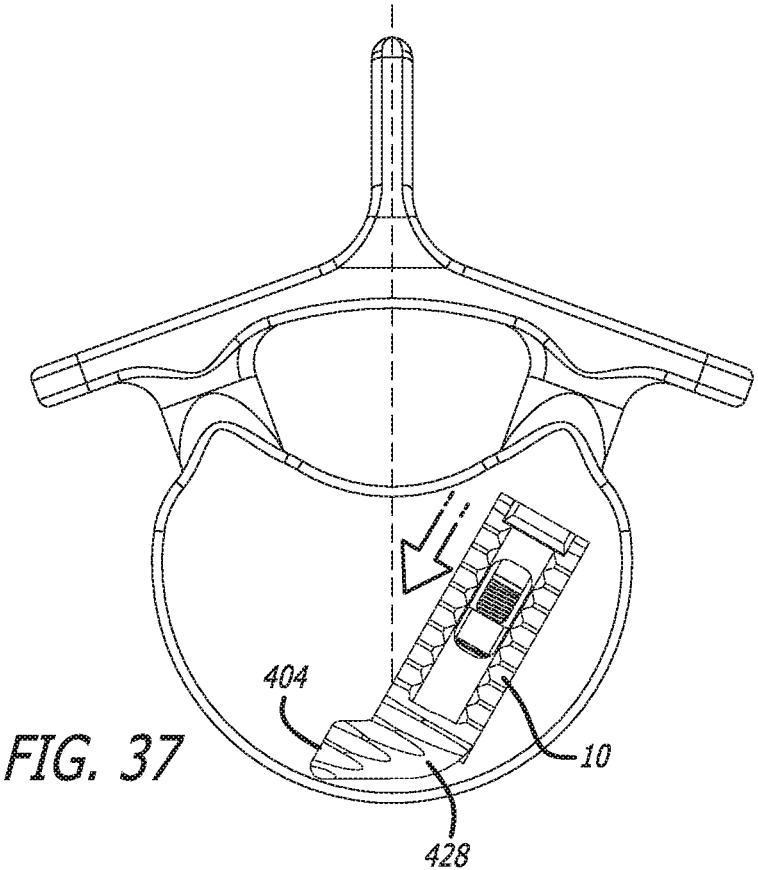
FIG. 37 is an upper view of one embodiment of an expandable spinal implant having an anterior projection and an anterior tip defining a distal end hook portion inserted into the disc space to a position proximate the apophyseal rim, and crossing over the midline of the disc space.

In one embodiment, as depicted in FIG. 37, the distal end hooked portion 404 is configured to be positioned in the disc space between the upper and lower vertebral bodies at a position crossing the midline ML of the disc space.

Figure 38:
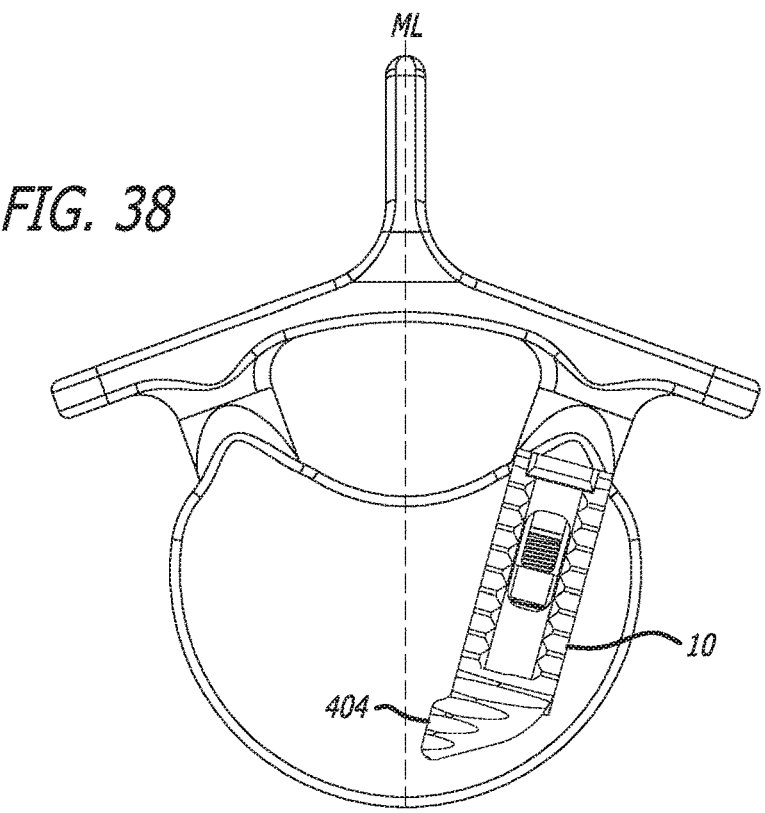
FIG. 38 is an upper view of one embodiment of an expandable spinal implant having an anterior projection and an anterior tip defining a distal end hook portion inserted into the disc space and spaced laterally away from the midline of the disc space.

In one embodiment of the invention, as depicted in FIG. 38, the distal end hooked portion 404 is configured to be positioned in the disc space between the upper and lower vertebral bodies at a position spaced laterally to one side of the midline ML of the disc space.

Figure 39:
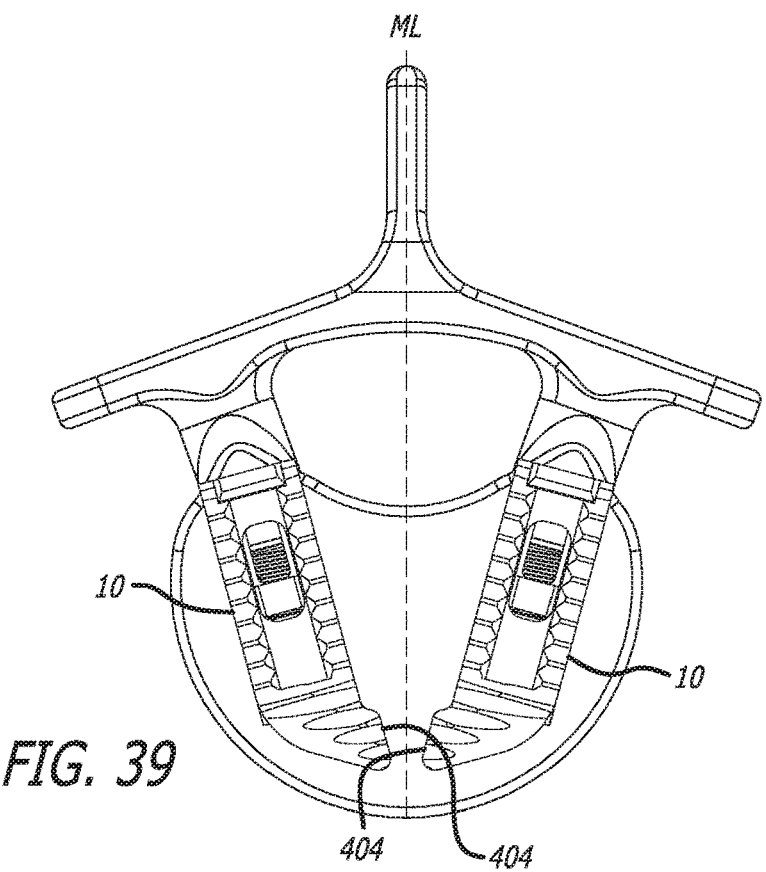
FIG. 39 is an upper view of two expandable spinal implants inserted into a disc space, each implant having an anterior projection and an anterior tip defining a distal end hook portion inserted into the disc space and spaced laterally away from the midline of the disc space.

In one embodiment of the invention, as depicted in FIG. 39, a pair of expandable implants 10 is configured to be positioned in the disc space between the upper and lower vertebral bodies, each respective implant 10 being located at a position spaced laterally to opposite sides of the midline ML of the disc space.

In one embodiment of the invention, as depicted in FIG. 31 the endplates include opposing respective sidewalls 423/424. The endplate sidewalls 423/424, with the frame sidewalls 102/104 and the proximal wall 110 define an enclosed area to hold bone growth material inserted into the implant 10 via the proximal aperture 111.

In one embodiment of the invention, as depicted in FIG. 29, the distal head 135 of the plug 130 abuts against a distal wedge portion 426. As the distal wedge portion 426 is pushed toward the proximal end of the implant 10, it pivots the first endplate 140 away from the second endplate 150, expanding the implant 10 to the expanded position.

In one embodiment of the invention, as depicted in FIGS. 31-39, the distal end beveled portion 406 intersects with one of the side walls 423/424 of the frame 100 opposite the distal end hooked portion 404, defining a distal end arcuate portion 428. The distal end arcuate portion 428 and the distal end beveled portion 406 together reduce a profile of insertion into the disc space of the implant 10.

In one embodiment of the invention, as depicted in FIG. 33, the distal end arcuate portion 428 allows the implant 10 to obtain greater lateral bony contact which is closer to the harder lateral vertebral rim, and to provide a greater medial grafting area.

Figure 40:
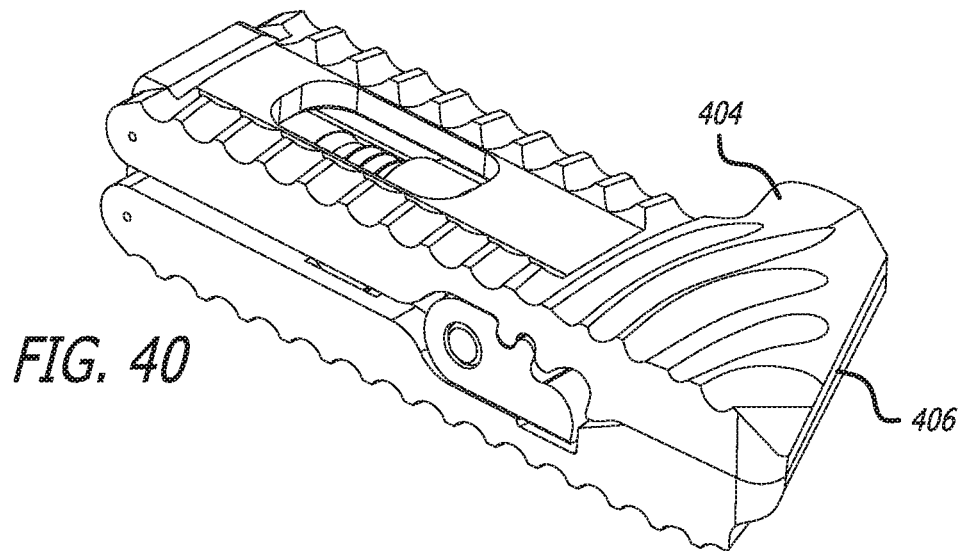
FIG. 40 is a perspective view of one embodiment of an expandable spinal implant having an anterior projection and an anterior tip defining a distal end hook portion in an orientation that is reversed from the orientation depicted in previous embodiments.
Figure 41:
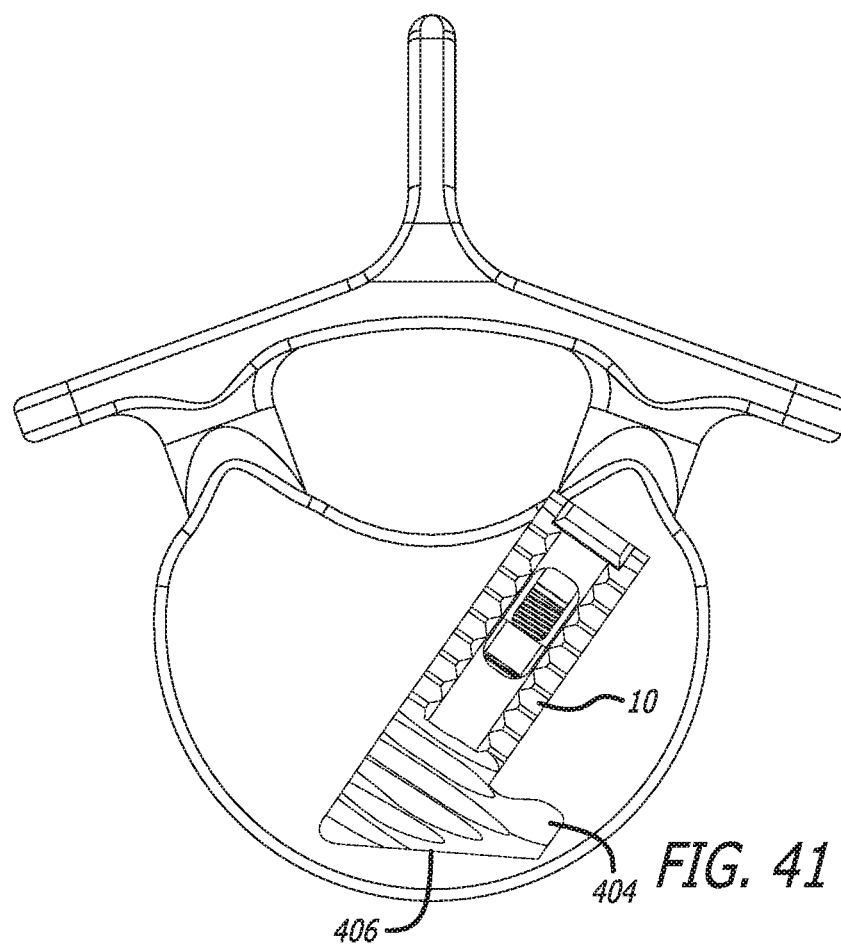
FIG. 41 is an upper view of the expandable spinal implant of FIG. 40 being inserted into the disc space toward the apophyseal rim.

In one embodiment of the invention, as depicted in FIGS. 40 and 41, the orientation of the distal end hooked portion 404 is reversed to extend from the opposite side of the implant 10. In this embodiment, as depicted in FIG. 41, the implant 10 contacts both the anterior rim and the posterior rim, providing improved stabilization of the adjacent vertebral bodies.

In some embodiments, the use of microsurgical, minimally-invasive and image guided technologies may be employed to access, view and repair spinal deterioration or damage, with the aid of spinal implant system 10, 30. Upon completion of the procedure, the non-implanted components, surgical instruments and assemblies (such as insertion instrument 30) of spinal implant system 10, 30 may be removed and the incision is closed. In some embodiments, the various instruments (such as the insertion instrumentation disclosed generally herein in FIG. 9 and related figures) disclosed may be provided with fiducial markers or other elements suitable for use with surgical navigation systems (including, but not limited to the STEALTHSTATION® Navigation system available from Medtronic plc), such that a surgeon may view a projected trajectory or insertion pathway of the implants 10, 20 relative to a patient's anatomy in real time and/or in near-real time.

It will be understood that the various independent components of the expandable spinal implants 10, 20, systems and insertion instruments 30 described herein may be combined in different ways according to various embodiments.

As a non-limiting example, the notches 114 shown in FIGS. 5-8 with respect to implant 20 may also be added to a proximal end of the implant 10 shown in FIGS. 1-4. As a further non-limiting example, the dual apertures 241a, 241b, 251a, 251b shown in FIGS. 5-8 with respect to the endplates 240, 250 of implant 20, may also be added to the endplates 140, 150 of the implant 10 shown in FIGS. 1-4.

It will be understood that various modifications may be made to the embodiments disclosed herein. Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed is:

1. An expandable spinal implant deployable between a collapsed position and an expanded position in a disc space between upper and lower vertebral bodies, the expandable spinal implant comprising:

a frame comprising an upper surface and a lower surface, a frame proximal end having a proximal wall, and a frame distal end having a distal wall, the frame proximal end having a proximal end width, and the frame defining a central longitudinal axis, a distal aperture being defined in the distal wall;

a plug movably disposed in the distal aperture and configured for movement from a position intermediate a proximal end and a distal end of the implant toward the distal end of the implant, the plug including a head portion including at least a first lateral post portion and at least a second lateral post portion;

a first endplate portion pivotally engaged with the frame and configured to expand outward from the frame when the plug is moved in a distal direction, the first endplate portion including an upper surface, a first endplate portion proximal end, a first endplate portion distal end, a first endplate portion first lateral surface extending between the first endplate portion proximal end and the first endplate portion distal end, an opposing first endplate portion second lateral surface extending between the first endplate portion proximal end and the first endplate portion distal end, and at least a first channel formed in the first endplate portion adjacent the first endplate portion first lateral surface, the at least a first channel being configured to receive the at least a first lateral post portion;

a first distal end portion extending outwardly from the first endplate portion including a first side surface, a second side surface, and a first tip portion, the first side surface of the first distal end portion extending from the first tip portion to the first endplate portion first lateral surface, and the second side surface of the first distal end portion extending from the first tip portion to the first endplate portion second lateral surface;

a second endplate portion pivotally engaged with the frame and configured to expand outward from the frame when the plug is moved in the distal direction, the second endplate portion including a lower surface, a second endplate portion proximal end, a second endplate portion distal end, a second endplate portion first lateral surface extending between the second endplate portion proximal end and the second endplate portion distal end, and an opposing second endplate portion second lateral surface extending between the second endplate portion proximal end and the second endplate portion distal end, and at least a second channel formed in the second endplate portion through the second endplate portion first lateral surface, the at least a second channel being configured to receive the at least a second lateral post portion;

a second distal end portion extending outwardly from the second endplate portion including a first side surface, a second side surface, and a second tip portion, the first side surface of the second distal end portion extending from the second tip portion to the second endplate portion first lateral surface, and the second side surface of the second distal end portion extending from the second tip portion to the second endplate portion second lateral surface;

wherein the at least a first channel extends in a first plane that is transverse to a mid-longitudinal axis of the first endplate portion, the at least a second channel extends in a second plane that is transverse to a mid-longitudinal axis of the second endplate portion, and movement of the plug toward the distal end of the implant, and corresponding interaction of the at least a first lateral post portion in the at least a first channel causes the first endplate portion and the first distal end portion to move away from the frame and interaction of the at least a second lateral post portion in the at least a second channel causes the second endplate portion and the second distal end portion to move away from the frame to move the implant from the collapsed position to the expanded position; and wherein the first distal end portion includes a mid-longitudinal axis that is transverse to the mid-longitudinal axis of the first endplate portion, and the second distal end portion includes a mid-longitudinal axis that is transverse to the mid-longitudinal axis of the second endplate portion.

2. The expandable spinal implant of claim 1, wherein when the implant is in the collapsed position, the first tip portion and the second tip portion further define a distal end beveled portion.

3. The expandable spinal implant of claim 2, wherein the implant is configured to be inserted in the disc space between the upper and lower vertebral bodies until the distal end beveled portions engage anterior apophyseal rims of each of the upper and lower vertebral bodies.

4. The expandable spinal implant of claim 1, wherein at least one of the first endplate upper surface and an upper surface of the first distal end portion comprises at least one first row of teeth defined thereon, and the second endplate lower surface and at least one of a lower surface of the second distal end portion comprises at least one second row of teeth defined thereon.

5. The expandable spinal implant of claim 1, wherein the frame further comprises at least one side wall engaged with the proximal wall and the distal wall, the side wall configured to space the proximal wall and the distal wall along a longitudinal axis of the expandable spinal implant.

6. The expandable spinal implant of claim 5, wherein the plug comprises a threaded outer surface, and wherein the distal aperture comprises a threaded inner surface operably engaged with the threaded outer surface of the plug.

7. The expandable spinal implant of claim 1, wherein the head portion of the plug is configured to contact portions of the first endplate portion and the second endplate portion to aid movement of the first endplate portion and the second endplate portion away from the frame when the plug is moved toward the distal direction.

8. The expandable spinal implant of claim 1, wherein movement of the plug away from the distal end in a proximal direction, and corresponding interaction of the at least a first lateral post portion in the at least a first channel causes the first endplate portion to move toward the frame and interaction of the at least a second lateral post portion in the at least a second channel causes the second endplate portion to move toward the frame to move the implant from the expanded position to the collapsed position.

9. The expandable spinal implant of claim 1, wherein each of the first endplate portion and the second endplate portion further comprise a first lateral side wall and a second lateral side wall spaced laterally apart from one another, the first lateral side wall of the first endplate portion extending in a first plane, the second lateral side wall of the first endplate portion extending in a second plane, and at least portions of the first distal end portion and the second distal end portion being located outside of the area between the first plane and the second plane.

10. An expandable spinal implant deployable between a collapsed position and an expanded position in a disc space between upper and lower vertebral bodies, the expandable spinal implant comprising:

a frame comprising an upper surface and a lower surface, a frame proximal end having a proximal wall, and a frame distal end having a distal wall, the frame proximal end having a proximal end width, and the frame defining a central longitudinal axis, a distal aperture being defined in the distal wall;

a plug movably disposed in the distal aperture and configured for movement from a position intermediate a proximal end and a distal end of the implant toward the distal end of the implant, the plug including a head portion including at least a first lateral post portion and at least a second lateral post portion;

a first endplate portion pivotally engaged with the frame and configured to expand outward from the frame when the plug is moved in a distal direction, the first endplate portion including an upper surface, an inner surface, a first endplate portion proximal end, a first endplate portion distal end, and at least a first channel formed in the first endplate portion, the at least a first channel being configured to receive the at least a first lateral post portion;

a first distal end portion extending outwardly from the first endplate portion including a first side surface, a second side surface, and a first tip portion, the first side surface of the first distal end portion extending from the first tip portion to the first endplate portion, and the second side surface of the first distal end portion extending from the first tip portion to the first endplate portion, a second endplate portion pivotally engaged with the frame and configured to expand outward from the frame when the plug is moved in the distal direction, the second endplate portion including a lower surface, an inner surface, a second endplate portion proximal end, a second endplate portion distal end, and at least a second channel formed in the second endplate portion, the at least a second channel being configured to receive the at least a second lateral post portion;

a second distal end portion extending outwardly from the second endplate portion including a first side surface, a second side surface, and a second tip portion, the first side surface of the second distal end portion extending from the second tip portion to the second endplate portion, and the second side surface of the second distal end portion extending from the second tip portion to the second endplate portion;

wherein the at least a first channel extends from a position adjacent the inner surface of the first endplate portion to a position spaced apart from the inner surface of the first endplate portion, and the at least a second channel extends from a position adjacent the inner surface of the second endplate portion to a position spaced apart from the inner surface of the second endplate portion, and movement of the plug toward the distal end of the implant, and corresponding interaction of the at least a first lateral post portion in the at least a first channel causes the first endplate portion and the first distal end portion to move away from the frame and interaction of the at least a second lateral post portion in the at least a second channel causes the second endplate portion and the second distal end portion to move away from the frame to move the implant from the collapsed position to the expanded position; and wherein the first distal end portion includes a mid-longitudinal axis that is transverse to a mid-longitudinal axis of the first endplate portion, and the second distal end portion includes a mid-longitudinal axis that is transverse to a mid-longitudinal axis of the second endplate portion.

11. The expandable spinal implant of claim 10, wherein at least one of the first endplate upper surface and an upper surface of the first distal end portion comprises at least one first row of teeth defined thereon, and the second endplate lower surface and at least one of a lower surface of the second distal end portion comprises at least one second row of teeth defined thereon.

12. The expandable spinal implant of claim 10, wherein the plug comprises a threaded outer surface, and wherein the distal aperture comprises a threaded inner surface operably engaged with the threaded outer surface of the plug.

13. The expandable spinal implant of claim 10, wherein the head portion of the plug is configured to contact the inner surfaces of the first endplate portion and the second endplate portion to aid movement of the first endplate portion and the second endplate portion away from the frame when the plug is moved toward the distal direction.

14. The expandable spinal implant of claim 10, wherein movement of the plug away from the distal end in a proximal direction, and corresponding interaction of the at least a first lateral post portion in the at least a first channel causes the first endplate portion to move toward the frame and interaction of the at least a second lateral post portion in the at least a second channel causes the second endplate portion to move toward the frame to move the implant from the expanded position to the collapsed position.

15. The expandable spinal implant of claim 10, wherein each of the first endplate portion and the second endplate portion further comprise a first lateral side wall and a second lateral side wall spaced laterally apart from one another, the first lateral side wall of the first endplate portion extending in a first plane, the second lateral side wall of the first endplate portion extending in a second plane, and at least portions of the first distal end portion and the second distal end portion being located outside of the area between the first plane and the second plane.

16. An expandable spinal implant deployable between a collapsed position and an expanded position in a disc space between upper and lower vertebral bodies, the expandable spinal implant comprising:
a frame comprising an upper surface and a lower surface, a frame proximal end having a proximal wall, and a frame distal end having a distal wall, the frame proximal end having a proximal end width, and the frame defining a central longitudinal axis, a distal aperture being defined in the distal wall;
a plug including a head portion, the plug being movably disposed in the distal aperture, and at least the head portion being moveable from a first position intermediate a proximal end and a distal end of the implant to a second position adjacent the distal end of the implant, the head portion including at least one lateral post portion;
a first endplate portion engaged with the frame, the first endplate portion including an upper surface, a first endplate portion proximal end, a first endplate portion distal end;
a first distal end portion extending outwardly from the first endplate portion including a first side surface, a second side surface, and a first tip portion, the first side surface of the first distal end portion extending from the first tip portion to the first endplate portion, and the second side surface of the first distal end portion extending from the first tip portion to the first endplate portion;
a second endplate portion engaged with the frame, the second endplate portion including a lower surface, a second endplate portion proximal end, a second endplate portion distal end;
a second distal end portion extending outwardly from the second endplate portion including a first side surface, a second side surface, and a second tip portion, the first side surface of the second distal end portion extending from the second tip portion to the second endplate portion, and the second side surface of the second distal end portion extending from the second tip portion to the second endplate portion;
wherein at least one of the first endplate portion and the second endplate portion is pivotally attached to the frame, and includes at least one lateral surface and at least one channel formed in the at least one lateral surface;
wherein the at least one channel is configured to receive the at least one lateral post, the at least one channel extending in a first plane that is transverse to a longitudinal axis of the implant, and movement of the plug toward the distal end of the implant, and corresponding interaction of the at least one lateral post portion in the at least one channel causes the one of the first endplate portion and the second endplate portion to move away from the frame to move the implant from the collapsed position to the expanded position; and
wherein the first distal end portion includes a mid-longitudinal axis that is transverse to a mid-longitudinal axis of the first endplate portion, and the second distal end portion includes a mid-longitudinal axis that is transverse to a mid-longitudinal axis of the second endplate portion.

17. The expandable spinal implant of claim 16, wherein the first distal end portion and the second distal end portion are each formed as a hooked end portion.

18. The expandable spinal implant of claim 16, wherein each of the first endplate portion and the second endplate portion further comprise a first lateral side wall and a second lateral side wall spaced laterally apart from one another, the first lateral side wall of the first endplate portion extending in a first plane, the second lateral side wall of the first endplate portion extending in a second plane, and at least portions of the first distal end portion and the second distal end portion being located outside of the area between the first plane and the second plane.

19. The expandable spinal implant of claim 1, wherein the first distal end portion and the second distal end portion are each formed as a hooked end portion.

20. The expandable spinal implant of claim 10, wherein the first distal end portion and the second distal end portion are each formed as a hooked end portion.

* * * * *